(12) United States Patent
Lindsay

(10) Patent No.: US 7,463,142 B2
(45) Date of Patent: Dec. 9, 2008

(54) RFID SYSTEM AND METHOD FOR TRACKING ENVIRONMENTAL DATA

(75) Inventor: Jeffrey D. Lindsay, Appleton, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 814 days.

(21) Appl. No.: 10/748,455

(22) Filed: Dec. 30, 2003

(65) Prior Publication Data
US 2005/0148828 A1 Jul. 7, 2005

(51) Int. Cl.
G08B 1/08 (2006.01)
G08B 13/14 (2006.01)
H04Q 7/00 (2006.01)

(52) U.S. Cl. .................... 340/539.12; 340/539.22; 340/539.26; 340/572.1

(58) Field of Classification Search . 340/539.1–539.32, 340/568.1–572.9
See application file for complete search history.

(56) References Cited

U.S. PATENT DOCUMENTS

| | | | |
|---|---|---|---|
| 4,656,463 A | 4/1987 | Anders et al. | |
| 5,047,614 A | 9/1991 | Bianco | |
| 5,164,707 A | 11/1992 | Rasmussen et al. | |
| 5,173,851 A | 12/1992 | Off et al. | |
| 5,361,070 A | 11/1994 | McEwan | |
| 5,380,991 A | 1/1995 | Valencia et al. | |
| 5,596,493 A | 1/1997 | Tone et al. | |
| 5,677,927 A | 10/1997 | Fullerton et al. | |
| 5,687,169 A | 11/1997 | Fullerton | |
| 5,689,240 A * | 11/1997 | Traxler ............... | 340/573.4 |
| 5,711,160 A | 1/1998 | Namisniak et al. | |
| 5,727,153 A | 3/1998 | Powell | |
| 5,798,694 A | 8/1998 | Reber et al. | |
| 5,832,035 A | 11/1998 | Fullerton | |
| 5,918,211 A | 6/1999 | Sloane | |
| 5,942,977 A | 8/1999 | Palmer et al. | |
| 5,955,969 A | 9/1999 | D'Hont | |

(Continued)

FOREIGN PATENT DOCUMENTS

| | | |
|---|---|---|
| DE | 29714999 | 11/1997 |
| DE | 19742126 | 3/1999 |
| WO | 0068851 | 11/2000 |
| WO | 0169429 A2 | 9/2001 |
| WO | 0215073 A1 | 2/2002 |
| WO | 0248955 A1 | 6/2002 |
| WO | 02080060 A1 | 10/2002 |
| WO | 0065532 A1 | 11/2002 |

OTHER PUBLICATIONS

Advertisement—www.mobilecloak.com—mCloak—RFID Tolltags Etc., Copyrighted—2002.

(Continued)

Primary Examiner—George A Bugg
Assistant Examiner—Jennifer Mehmood
(74) Attorney, Agent, or Firm—Dority & Manning, P.A.

(57) ABSTRACT

A method and system for tracking a body's bio-readings and environmental information in which such bio-readings are generated is disclosed. Conventional bio-reading sensor technology may be used in combination with technology for receiving information from electronic tags associated with items in a body's environment. Such technology may include RFID smart tags associated with items in an environment. Such smart tags store information describing the item associated with the smart tag. An RFID smart tag reader may be provided for retrieving item description information stored in such smart tags. The combination of bio-reading data and environmental data provide a power tool in evaluating behavioral and environmental variables that affect a body's bio-readings.

39 Claims, 8 Drawing Sheets

U.S. PATENT DOCUMENTS

| | | | |
|---|---|---|---|
| 5,990,794 | A | 11/1999 | Alicot et al. |
| 6,037,879 | A | 3/2000 | Tuttle |
| 6,100,806 | A * | 8/2000 | Gaukel ..................... 340/573.4 |
| 6,177,903 | B1 | 1/2001 | Fullerton et al. |
| 6,195,006 | B1 | 2/2001 | Bowers et al. |
| 6,198,394 | B1 * | 3/2001 | Jacobsen et al. ......... 340/573.1 |
| 6,218,979 | B1 | 4/2001 | Barnes et al. |
| 6,226,619 | B1 | 5/2001 | Halperin et al. |
| 6,249,227 | B1 | 6/2001 | Brady et al. |
| 6,294,997 | B1 | 9/2001 | Paratore et al. |
| 6,354,493 | B1 | 3/2002 | Mon |
| 6,386,450 | B1 | 5/2002 | Ogasawara |
| 6,407,665 | B2 | 6/2002 | Maloney |
| 6,409,086 | B1 | 6/2002 | Pellaumail et al. |
| 6,429,768 | B1 | 8/2002 | Flick |
| 6,435,407 | B1 | 8/2002 | Fiodelisi |
| 6,446,049 | B1 | 9/2002 | Janning et al. |
| 6,451,154 | B1 | 9/2002 | Grabau et al. |
| 6,491,217 | B2 | 12/2002 | Catan |
| 6,497,656 | B1 | 12/2002 | Evans et al. |
| 6,507,279 | B2 | 1/2003 | Loof |
| 6,579,231 | B1 * | 6/2003 | Phipps ....................... 600/300 |
| 6,587,835 | B1 | 7/2003 | Treyz et al. |
| 6,595,929 | B2 | 7/2003 | Stivoric et al. |
| 6,619,835 | B2 | 9/2003 | Kita |
| 6,640,214 | B1 | 10/2003 | Nambudiri et al. |
| 6,693,511 | B1 | 2/2004 | Seal |
| 6,693,539 | B2 | 2/2004 | Bowers et al. |
| 6,694,177 | B2 | 2/2004 | Eggers et al. |
| 6,707,376 | B1 | 3/2004 | Patterson et al. |
| 6,707,381 | B1 | 3/2004 | Maloney |
| 6,836,843 | B2 * | 12/2004 | Seroussi et al. ............. 713/173 |
| 6,977,586 | B2 * | 12/2005 | Martin et al. .......... 340/539.15 |
| 2002/0040321 | A1 | 4/2002 | Nicholson |
| 2002/0065680 | A1 | 5/2002 | Kojima et al. |
| 2002/0077906 | A1 | 6/2002 | Remler |
| 2002/0152119 | A1 | 10/2002 | Kepros et al. |
| 2003/0036957 | A1 | 2/2003 | Nguyen |
| 2004/0100376 | A1 * | 5/2004 | Lye et al. ............... 340/539.12 |

OTHER PUBLICATIONS

Advertisement—WWW.MOBILECLOAK.COM—RFID Tags, Copyrighted—2002.
Ultra-Wideband Technology for Short- or Medium-Range Wireless Communications, Copyrighted—2001 Intel Corporation.
Ultra Wideband: The Ultimate Disruptive Technology, WWW.ULTRAWIDEBANDPLANET.COM—Jun. 11, 2002—Int Media Group.
U.S. Approves Ultra-Wideband Technology, WWW.WIRELESSNEWSFACTOR.COM—Feb. 15, 2002.
New Public Safety Applications and Broadband Internet Access Among Uses Envisioned by FCC Authorization of Ultra-Wideband Technology, Federal Communications Commission—Feb. 14, 2002.
Ultra Wideband—searchnetworking.com, Copyrighted 2000-2002—Techtarget.
Internet Article—WWW.TIMEDOMAIN.COM—PulsON Technology Capabilities, Sep. 3, 2002.
White Paper—Integration of Auto-ID Tagging System with Holonic Manufacturing Systems—Cambridge University Auto-ID Center, Published—Sep. 1, 2001.
Auburn University—Detection & Food Safety Center—audfs.eng.auburn.edu, Sep. 4, 2002
Internet Article—Smart Tags Indicate Freshness—courses.che.umn.edu, Sep. 4, 2002.
Internet Article—WWW.AIMGLOBAL.ORG—Pharmaceutical Distributor Cuts Day of Safety Stock, Aug. 29, 2002.
Internet Article WWW.IDTECHEX.COM—Independent Market, Strategic and Technology Reports, Aug. 29, 2002.
Internet Article—WWW.READYMEALSINFO.COM—M&S Pilots RFID System for Fresh Food Operation, Sep. 4, 2002.
Internet Article—audfs.eng.auburn.edu—Auburn University Detection & Food Safety Center, Sep. 4, 2002.
RFID Journal—Internet Article—WWW.RFIDJOURNAL.COM—Auto-ID Center Opens Demonstration Lab in the U.K., Sep. 4, 2002.
Internet Article—WWW.AUTOIDCENTER.ORG—Transmitting ePC Codes, Aug. 26, 2002.
Internet Article—WWW.ELECTRONICIDINC.COM—Destron-Fearing Electronic ID Background, Sep. 4, 2002.
Internet Article—Destronfearing.com—Applications-Companion Animals, Sep. 4, 2002.
Internet Article—audfs.eng.auburn.edu—Auburn University—Detection & Food Safety Center, Sep. 4, 2002.
Internet Article—sfgate.com—Shops Try Chips for Tracking Every Move by Client 'Tribe' Monitoring Systems Note What Catches Customers' Eyes, Aug. 6, 2002.
Internet Article—WWW.AIMGLOBAL.ORG—Radio Frequency Identification—RFID A Basic Primer, Sep. 28, 1999.
Internet Article—WWW.AIMGLOBAL.ORG—Common Applications—RFID, Jul. 23, 2002.
Internet Article—WWW.USATODAY.COM—New Chips Could Make Everyday Items 'Talk', Jul. 23, 2002.
Forbes Magazine—The Internet of Things, Mar. 18, 2002.
Auto-ID Center—Institute for Manufacturing, University of Cambridge—White Paper—Auto-ID Based Control—An Overview, Feb. 1, 2002.
Wireless Handhelds—Beam Up Some Information, Scotty, Control Engineering, May 2002.
Scientific American—Wireless Data Blaster, May 2002.
Auto-ID Center, Institute for Manufacturing, University of Cambridge, White Paper—The Intelligent Product Driven Supply Chain, Feb. 1, 2002.
Auto-ID Center Massachusetts Institute of Technology—White Paper—Smart Medicine—The Application of Auto-ID Technology to Healthcare, Feb. 1, 2002.
"Theory, History, and the Advancement of Parametric Loudspeakers: A Technology Overview", by James J. Croft and Joseph O. Norris, Revision D, American Technology Corporation, San Diego,CA 2002. Available at http://www.atcsd.com/pdf/HSSWHTPAPER-RevE.pdf.
Popular Science, What's New, Suzanne Kantra Kirschner, We've heard hypersonic sound. It could change everything. Exemplary applications of hypersonic technology are illustrated at www.popsci.com/popsci/hometech/article/0, 12543,351353,00.html.
D. McFarlane, "Auto-ID Based Control," White Paper for the Auto-ID Centre Institute for Manufacturing, University of Cambridge, Cambridge, United Kingdom, Feb. 1, 2002. Available at http//www.autoidcenter.org/research/CAM-AUTOID-WH-004.pdf.
Wincor Nixdorf, Member of METRO Group, Future Store Initiative, "Store Vision—High-Tech for the Future in Retail," Wincor Vision May 2003. Available at http:/www.wincor-nixdor.com/internet/com/Idustries/Retail/WincorVision/
WincorVisionSpezialFSI,templated=blob.jsp.property=Data.pdf.
Amskan Editorials, RFID Overview: The science of evaluating RFID (Radio Frequency Identification) Technology, Amskan Update: Jan. 1999. Available at www.amskan.com/html/rfid_overview.html.
Ludwig Weimann and Junru Wu Transdermal Drug Delivery by Sono-Macroporation http://ultra-sonictechnologies.com/cancun-presentation.htm Nov. 4, 2003 11:28:14 AM.
A Sensate Liner for Personnel Monitoring Applications, Dr. Eric J. Lind et al.
U.S. Appl. No. 10/748,691, filed Dec. 30, 2003.
U.S. Appl. No. 10/748,763, filed Dec. 30, 2003.
U.S. Appl. No. 10/748,118, filed Dec. 30, 2003.

* cited by examiner

RFID SYSTEM AND METHOD FOR TRACKING ENVIRONMENTAL DATA

TECHNICAL FIELD OF THE INVENTION

The present invention relates to novel implementations of Radio Frequency Identification Device (RFID) technology for tracking environmental data describing the environment in which a body's bio-readings are being monitored.

BACKGROUND

Advances in miniaturization technology have resulted in the development of increasingly small electronic devices for sensing a diverse array of quantities. Similar advances in wireless communication technologies combined with the increased popularity of interconnected computer systems, such as the Internet, provide the technology necessary to cost effectively transfer vast amounts of data between two or more computers. The combination of such technologies provide the ability to use small bio-sensors to monitor and track a body's bio-readings as well as the activity level and environmental conditions in which such bio-readings are generated and to transfer such data between computers and computer networks.

One area in particular where such technology is well suited is in the medical field. Monitoring and recording human bio-readings, human activity, as well as the environmental conditions in which such readings are generated, can provide insight into the causes of certain medical conditions. In addition, such monitoring may be used to determine the effectiveness of medical treatments and to enhance the effectiveness of such treatments. As a result, personalized human body monitoring devices have been developed.

Body monitoring devices have been developed that are said to have the ability to measure a number of physiologic parameters (bio-readings) that allow health researchers and professionals, as well as individuals, to continuously and more accurately track physical activity and energy expenditure. Such prior art systems are said to be able to accurately monitor heat flow, galvanic skin response, skin temperature, near body ambient temperature, heart beat and transfer such data to a remote computer for analysis. Algorithms have also been developed said to be capable of integrating multiple physiological variables from developed said to be capable of integrating multiple physiological variables from the wearable sensor to predict calories burned, length in time of exercise, number of steps taken, resting energy expenditure, active energy expenditure, sleep onset, wake time and sleep duration.

One problem with such prior art monitoring systems, however, is that these systems have a very limited ability to directly monitor and record information about the environment in which a body's bio-readings are being monitored. For example, such systems may be able to record near skin temperatures, air quality, sound quality (climatic data) and global positioning system data (geographical data); however, such prior art systems do not have the ability to automatically record detailed information about items a body's environment in which bio-readings are generated.

It is well known that a person's environment, including items within an environment, can affect the person as well as the bio-readings of such person. Stated another way, recording the environmental parameters in which a person's bio-readings are generated puts such bio-readings in context. A heart rate of 160 beats per minute may not be alarming when a person is on a treadmill but such a heart rate might well be alarming if the person is in a bed sleeping. Tracking items within an environment (i.e. bed, treadmill, etc.) would provide the ability to determine which of the above two situations applies to a particular set of monitored data.

Therefore, there is a need for monitoring systems that have the ability to automatically track items within an environment in which bio-readings are being generated.

Another problem with the previously described prior art systems is that they do not warn a user (a body being monitored) of an environmental condition that may pose a danger to the well being of the user. For example, everything electronic consumes electrical power and electrical power is generated through the flow of electrical current. The flow of electrical current creates electromagnetic fields, and more importantly, stray electromagnetic fields (assuming imperfect shielding). Stray electromagnetic fields can have an adverse influence on the operation of electronic equipment. For example, microwave ovens and electric drills can generate strong electromagnetic fields that have been known to make pacemakers malfunction. Another example of a dangerous environment would be a wet floor. The presence of a mop might indicate the possibility of a wet floor. Such conditions can be particularly dangerous for the visually impaired who do not have the ability to visually inspect an environment. Therefore, there is a need for a monitoring system and can monitor environmental conditions and warn a person of a potentially dangerous environment.

Thus, a need exists for an improved body and environment monitoring system that will address at least certain of the drawbacks and limitations of conventional systems, and offer benefits not achievable with the present systems.

SUMMARY

Objects and advantages of the invention will be set forth in the following description, or may be obvious from the description, or may be learned through practice of the invention.

The term "bio-sensor data" or "bio-sensor signals" refers generally to sensor data/signals relating to biological readings (bio-readings) for a physiological parameter associated with an organism, such as the body of a mammal. In some cases, bio-sensor data is representative of a physiological parameter. In other cases, bio-sensor data is used by a computing device to calculate data representative of a physiological parameter. Exemplary body parameters include vital signs, blood sugar level, skin resistance, etc. and, as noted above, may be monitored directly through the appropriate sensor technology or may be derived through mathematical calculations using bio-sensor data.

Broadly speaking, environmental data refers to data that describes an environment. An environment may be described using terms such as temperature, humidity, pressure, weather (climatological data). An environment by be described by its location using geographical data such as GPS data. The term environmental-data, as used herein, does not include geographical data or climatological data unless noted otherwise.

An environment may also be described by the items within such environment. Exemplary environmental-data includes model numbers, serial numbers, item descriptions, warning codes, EMI codes, etc. associated with items located in an environment. In addition, environmental-data may include room codes, building codes, vehicle codes, etc. for structures that may define the immediate boundaries of an environment. Such environmental-data may be stored in electronic tags associated with an item in an environment. Thus, as used herein, environmental-data is simply data that may be used to describe items in an environment or data that is used to retrieve item descriptions. It should be noted that GPS (global positioning system) type-data that is stored in electronic tags may be considered environmental-data. While GPS type data stored in electronic tags may provide the same information as GPS data derived from satellite signals, electronic tag GPS data is fundamentally different that GPS data derived from satellite signals.

As previously noted, measuring and recording a body's bio-readings alone provides only part of the picture as to the meaning of such data. A properly designed monitoring system according to aspects of the present invention will provide significant improvements to prior art monitoring systems by also monitoring environmental conditions and providing detailed environmental data relating to the environment in which bio-readings are generated by a body.

One aspect of the present invention relates generally to novel implementations of Radio Frequency Identification Device (RFID) technology for providing environmental data that describes the environment in which a body's bio-readings are being monitored. Radio Frequency Identification Devices and associated systems are well suited for monitoring applications. RFID systems may include low-cost, passive "smart" chips or "tags" that can be embedded in or attached to items to convey information about the item via a smart tag scanner/reader. Smart tags are generally small label-like devices with a micro-chip and a miniature embedded antenna. Such tags may be passive or active, the active tags requiring an internal power supply. A reader/scanner interrogates the smart tag with an electronic "trigger" signal. The smart tag in turn generates an electromagnetic pulse response that is readable by the scanner, the response containing the item information. RFID smart tags can be embedded in or attached to an item's packaging, may be incorporated directly into the item, may be attached to walls, floors, doors, steps, etc. and may convey conventional "bar code" information, as well as other more detailed information.

The disclosed exemplary RFID technology and associated systems provide the ability to reliably and automatically obtain real-time information about individual items throughout a particular environment. Such data may then be transferred to a display, a local computing device and/or remote computing device. Environmental data is ideally recorded substantially simultaneously with the generation and recording of a body's bio-readings.

Another benefit of one possible embodiment of the present invention relates to safety. A properly configured monitoring system provides the ability to warn a body/user or remote computer of potential hazards such as devices that can interfere with the proper operation of medical devices associated with a body. An RFID based environment tracking system can direct a person to an exit door in a smoke filled room or to a fire extinguisher that may be behind a nearby wall. Such functionality is of particular importance for those with visual impairments who lack the ability to visually examine an environment. A RFID based environment tracking system according to one embodiment of the disclosed invention can even inform a visually impaired person how many steps she must walk up or down to reach the top or bottom of a staircase or that she just walked past a door to a bathroom and give her the opportunity to electronically mark the location of such bathroom.

Further benefits of tracking environmental data relate to detecting items that can have an adverse affect on the accuracy of bio-readings. As previously noted, electromagnetic fields can have an adverse affect on the operation of electronic equipment. As electronics in general, and bio-sensors in particular, become smaller and smaller, they become more susceptible to stray electromagnetic fields. When inaccurate bio-readings are suspected or detected, a user can access the environmental data for the time such bio-readings were taken and look for items that are likely suspects for generating stray electromagnetic fields that could cause such spurious bio-reading data.

Even further benefits can be gained by linking a RFID base environment monitoring system to a computer network, such as the Internet. Using the Internet in conjunction with the present invention allows a remote party to monitor the health and alertness of a user or group of users. For example, the blood alcohol content of a truck driver could be monitored and/or a truck driver's environment could be monitored for alcoholic beverage containers, wherein such monitoring occurs remotely and in real-time. In addition, a truck driver could be monitored for alertness. In addition, a properly configured monitoring system according to aspects of the present invention can be used to track groups of bodies, such as workers and athletes.

Yet another benefit of one embodiment of the present invention relates to issuing alerts to a remote party. For example, a person who falls and breaks bones may become incapacitated or otherwise not be able request assistance. Remote monitoring of a body's bio-readings alone may not be sufficient to detect such a life threatening condition/situation. Through the monitoring of environmental data, however, the disclosed monitoring system can be configured to provide the ability to detect such a life-threatening conditions and to timely dispatch emergency personnel to the user's location. Additionally, a user's environment, such as a medicine cabinet, may be quickly and remotely scanned for medication or other therapeutic/pharmaceutical remedies that could be administered in emergency situations while waiting for help to arrive.

Still another benefit of one embodiment of the present invention relates to the administration of therapeutic and/or pharmaceutical treatments. The monitoring system may be configured to transmit treatment signals that result in the administration of an insulin treatment, for example, when a body's blood sugar level exceeds a predefined level. Similarly, a room's environmental controls may be adjusted in response to a body's temperature data or a bed's positioning controls may be adjusted in response to body's pressure data or a timed schedule. The monitoring system may be additionally configured to scan the environment to obtain identification information from the relevant treatment control systems so that the monitoring system can automatically generate properly configured treatment-signals. Such functionally may be of particular importance, for example, in hospitals having numerous drug delivery systems, bed positioning system and climate control systems.

In one related embodiment, the monitoring system can assist in predicting impending release of body wastes, incorporating, for example, biosensor systems such as those disclosed in U.S. Pat. No. 6,407,308, titled: "Disposable Article Having Sensor to Detect Impending Elimination of Bodily Waste," and issued Jun. 18, 2002 to Roe et al., and such patent is herein incorporated by reference to the extent it is non-contradictory herewith. Such systems can be adapted for the benefit of people in hospitals, nursing homes, day care centers, or at home, including those struggling with incontinence or bed wetting problems Yet another advantage of one embodiment of the present invention relates to accumulating bio-reading reference data. Bio-reading reference data may comprise body specific average values, peak values, minimum values, etc. as well as "average human" values. The body specific heart rate for a particular human male may be 76 beats per minute as calculated over a period of time whereas the "average human" 42 year old male heart rate may be 72 beats per minute. Such reference data may be presented to a user along with current bio-reading data and environmental data to enhance the understanding of current bio-reading data and the possible influence the current environmental conditions may be having on a body.

In one particular embodiment of the present invention, a body and environment monitoring system comprises at least one bio-sensor associated with a body and configured to generate signals representative of at least one body-parameter (bio-reading). Examples of body-parameters may include body temperature, blood pressure, heart rate, blood sugar level, blood oxygen level, cholesterol level, respiration rate, hormone level (detection), galvanic skin response, EMG, EEG, EOG, body fat, hydration level, activity level, body position, UV radiation exposure and UV radiation absorption. A first computer is associated with the body and is configured to retrieve sensor-data from at least one bio-sensor. In addition, at least one electronic tag scanning device is provided for retrieving information from electronic tags associated with items in the surrounding environment. One possible embodiment of an electronic tag scanning device is an RFID STR device and one possible electronic tag is an RFID smart tag. The electronic tag scanning device may be configured to scan the environment around a body and retrieve at least part of the information stored in electronic tags within communication range of the electronic tag scanning device thereby obtaining environmental-data. Exemplary environmental-data includes an item identification number, item model number, warning code, EMI Code, room code, floor code, building code, vehicle code, meal code and nutrition code.

The first computer may be further configured to process sensor-data generated by bio-sensors and to automatically generate treatment-signals when such sensor-data indicates that a body-parameter meets predefined criteria. For example, the first computer may monitor a body's blood sugar level and generate treatment-signals that instruct a drug delivery system to administer an insulin injection when a blood sugar level exceeds a predefined level.

The at least one electronic tag scanning device may be further configured to communicate with the first computer and to transfer at least part of the received environmental-data to the first computer. The first computer may compare such environmental-data to a list of equipment known to be dangerous to the body being monitored (or known to be dangerous to bodies in general) and issue a warning to the body (user) and/or a remote computer when a dangerous item has been detected. Exemplary warning messages include a beep, text message, voice message and flashing light. Alternatively, a user may have a list of items he wishes to track and be notified when such items are detected in his environment.

The present embodiment may also comprise a user display configured to display at least part of the processed and/or unprocessed sensor-data and environmental-data. The displayed sensor-data may represent any combination of real-time data, average-data, high-peak data, low-peak data, etc., where average-data, high-peak data and low-peak data are examples of reference data. Average person data (described in detail later) may also be displayed. The display may comprise a personal digital assistant, a watch, a LCD screen or any other suitable display device associated with the system. Such display may be in wired and/or wireless communication with either or both of the first computer and electronic tag scanning device depending on the system configuration desired.

The first computer may also be in communication with a local area network (LAN) such as an intranet or a wide area network (WAN) such as the Internet. Through such communications mediums, sensor data and environmental data can be transferred to remote computers and monitored in real-time by a human or a computer executing a monitoring program.

In yet another embodiment of a monitoring system according to aspects of the present invention, at least one electronic tag scanning device is associated with a body, wherein the at least one electronic tag scanning device is configured to listen for electronic tag signal transmissions comprising environmental-data. Such electronic tag scanning device may be attached to a body, mounted on a body or carried by a body. The electronic tag scanning device may be further configured to transmit an electronic tag trigger signal when a predefined amount of time elapses with no valid electronic tag transmissions being detected. The electronic tag scanning device may also be configured to transmit an electronic tag trigger signal according to transmit-criteria where said transmit-criteria is at least one member from the group consisting of: (1) periodically at set intervals; (2) periodically at random intervals; (3) upon manual request by a user; and (4) automatic request issued by a computer.

The electronic tag scanning device may be an RFID STR device and the electronic tag may be an RFID smart tag. The electronic tag scanning device may be in communication with a remote computer and may transfer at least part of the environmental-data to such remote computer.

The system may issue a warning message to the user and/or a remote computer when environmental-data received from electronic tags meets predefined warning-criteria. The monitoring system may further comprise a display that may be configured to display information received form at least one of said electronic tag scanning device and said remote computer and wherein said display may be further configured to display at least one of said environmental data and said warning message.

The monitoring system may further comprise a computer configured to retrieve sensor-data from at least one bio-sensor associated with a body. Such computer may be a Bio-Reading & Environmental Monitor (BREM) computer configured to automatically generate treatment-signals when a sensor-data indicates that a monitored body-parameter meets predefined treatment-criteria.

A still further embodiment of a body monitoring system according to certain aspects of the present invention comprises a first computer adapted to either mount on a body, attach to a body or be carried by a body. Such first computer may be configured to retrieve sensor-data from at least one bio-sensor associated with a body wherein said bio-sensor is configured to generate sensor-data for at least one body-parameter. The first computer may be further configured to generate treatment-signals and to transmit such treatment-signals to a treatment control system when the first computer determines that a body-parameter meets predefined treatment criteria. The first computer may be configured to automatically determine the proper treatment-signal format necessary to cause a control system to administer the appropriate treatment. Such auto-configuration function may be based at least in part on treatment-control-system-information retrieved from said treatment control system via wireless technology such as Wi-Fi or Bluetooth.

The body monitoring system may further comprise at least one electronic tag scanning device configured to retrieve information stored in electronic tags associated with items in an environment. Such electronic tag scanning device may be configured to communicate with the first computer, wherein the electronic tag scanning device may be configured to scan an environment and to retrieve at least part of the information stored in an electronic tag associated with a treatment control system thereby obtaining treatment-control-system-information. Such treatment-control-system-information may be used by said first computer when performing the above-described auto-configuration function.

Still further embodiments of the present invention relate to methodologies for tracking environmental-data comprising the steps of configuring an electronic tag scanning device to listen for electronic tag transmissions and transmitting a trigger signal when no electronic-tag transmissions are received during a predefined period of time. The trigger signal is configured to cause electronic tags to generate electronic-tag transmissions wherein such transmissions comprise environmental-data. The trigger signal may also be transmitted according to predefined transmit-criteria. Exemplary transmit-criteria may include any combination of: (1) periodically at set intervals; (2) periodically at random intervals; (3) upon manual request by a user; and (4) automatic request issued by a computer. The received environmental-data may be stored in timed-stamped memory and initially classified as untracked data pending evaluation. Such environmental-data may then be evaluated to determine if said environmental-data should be reclassified as tracked data.

Still further embodiments of the present invention relate to methodologies for monitoring items in an environment comprising the steps of obtaining environmental-data from electronic tags associated with items in a user's environment. Next, warning-criteria may be accessed and compared to the environmental-data. If the environmental-data describes an item that is consistent with an item description provided by the warning-criteria, a warning message may be issued to a user. The warning message may be at least one member from the group consisting of: (1) a beep; (2) an voice message; (3) a flashing light; (4) a message displayed on a display; (5) a vibration or other tactile signal, and (6) a message printed in Braille. The warning message may include: (1) a description of the item; (2) the location of the item; and (3) a description of the warning.

Additional embodiments of the present subject matter may include and incorporate various combinations of aspects, features, or parts referenced in the summarized objectives above, and/or features or components as otherwise discussed in this application.

Those of ordinary skill in the art will better appreciate the features and aspects of such embodiments, and others, upon review of the remainder of the specification.

BRIEF DESCRIPTION OF THE DRAWINGS

A full and enabling description of the present subject matter, including the best mode thereof, directed to one of ordinary skill in the art, is set forth in the specification, which makes reference to the appended figures, in which.

Figure 1:
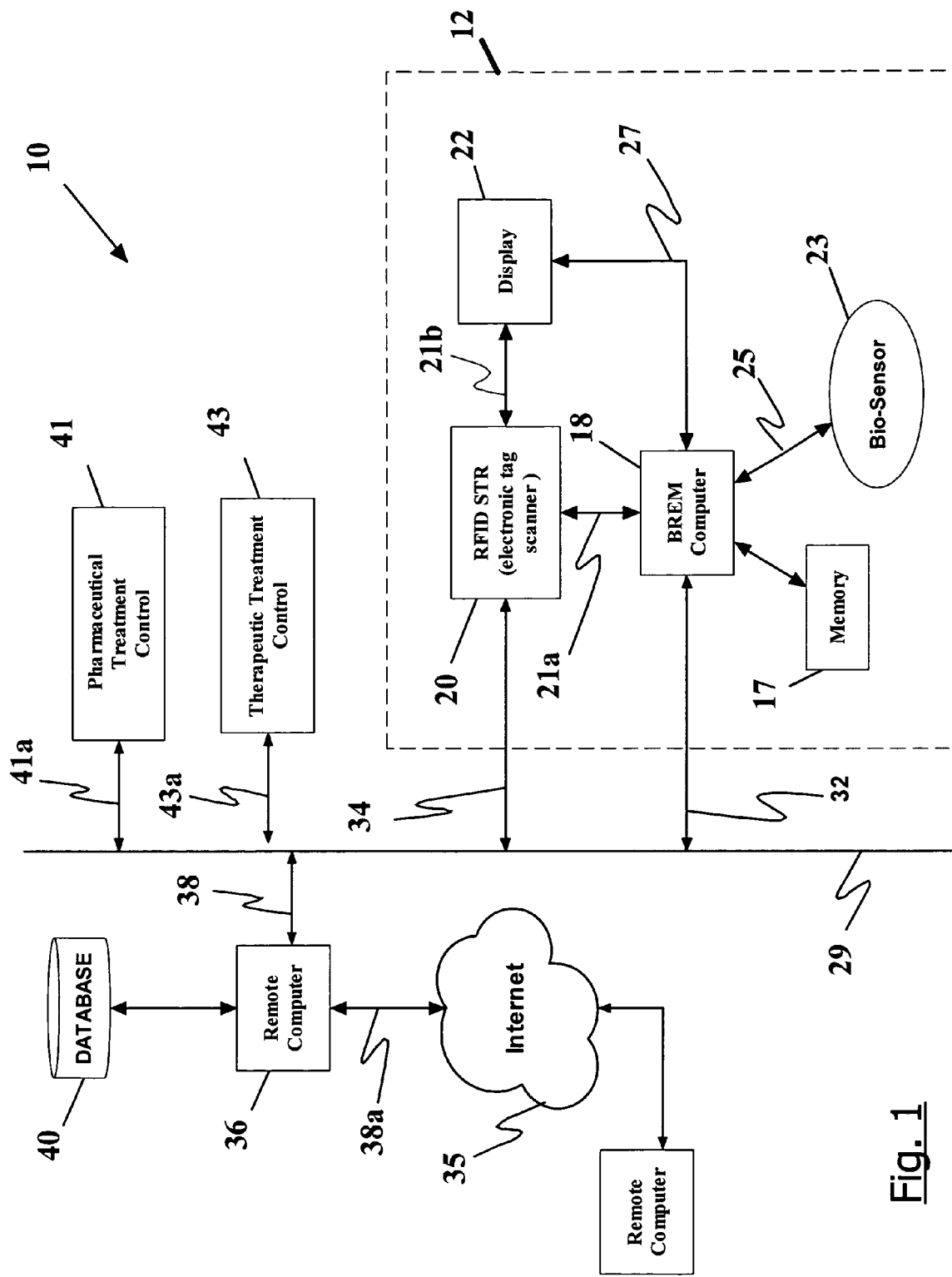
FIG. 1 is a block diagram illustration of an exemplary bio-reading and environment monitoring system in accordance with one possible embodiment of the invention.

Repeat use of reference characters throughout the present specification and appended drawings is intended to represent same or analogous features or elements of the present technology.

DETAILED DESCRIPTION

Reference will now be made in detail to one or more embodiments of the invention, examples of which are graphically illustrated in the drawings. Each example and embodiment are provided by way of explanation of the invention, and not meant as a limitation of the invention. For example, features illustrated or described as part of one embodiment may be utilized with another embodiment to yield still a further embodiment. It is intended that the present invention include these and other modifications and variations.

Figure 2:
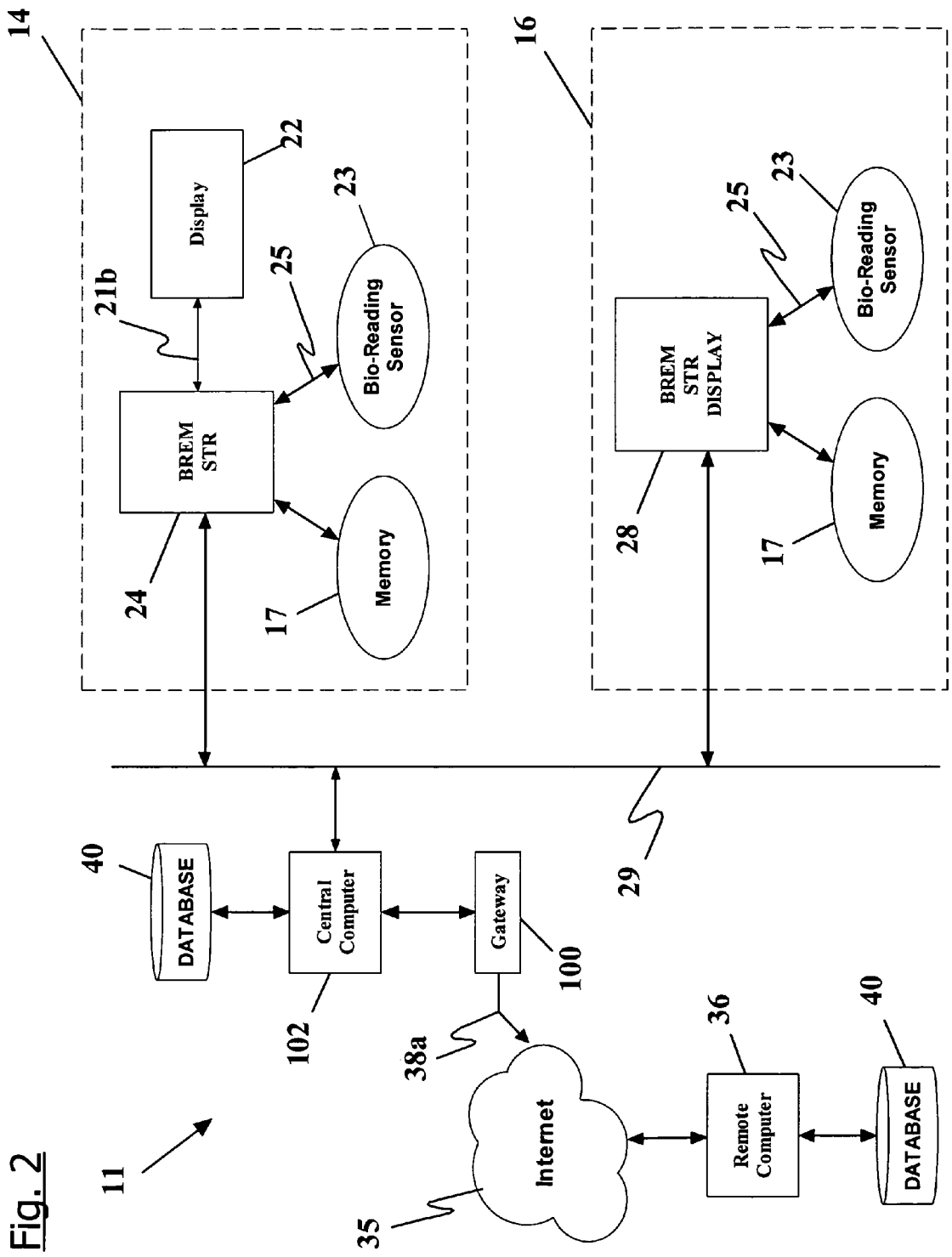
FIG. 2 is a block diagram illustration of an exemplary bio-reading and environment monitoring system in accordance with alternative embodiments of the invention.

FIG. 1 and FIG. 2 are block diagram illustrations of exemplary bio-reading and environment monitoring systems in accordance with exemplary embodiments of the present invention. System 10 depicts exemplary BREM 12 configuration and system 11 depicts BREM 14 and BREM 16 configurations. For BREM 12, BREM computer 18, radio frequency identification (RFID) smart tag reader (STR) and display 22 are separate components. For BREM 14, BREM computer 18 and RFID STR 20 have been integrated into one component, BREM/STR 24. For BREM 16, BREM computer 18, RFID STR 20 and display 22 have been integrated into one component, BREM/STR/Display 28. The attributes of the exemplary components of BREM 12 will be discussed below, however, it should be appreciated that the remarks relating to the individual components of BREM 12 also generally related to the integral components of BREM 14 and BREM 16.

BRME 12 comprises an exemplary BREM computer 18, electronic tag scanner 20, bio-sensors 23 and display 22. BREM computer 18 may be associated with a body and may be configured to communicate with electronic tag scanner 20, display 22 and bio-sensors 23 through wired or wireless communications links 21a, 27 and 25 respectively. Exemplary wireless technologies are well known in the art and may include technologies such as Wi-Fi and Bluetooth.

Bio-sensors are generally defined as devices configured to generated signals related to biological readings (bio-readings) for physiological parameters associated with an organism, such as a human. In some cases, unprocessed bio-sensor data is representative of a physiological parameter. In other cases, bio-sensor data is used by a computing device to calculate data representative of a physiological parameter. The monitored body may be the body of any mammal; however, in the descriptions presented below, the body will be a human body.

Exemplary body parameters may include any combination of: (1) body temperature; (2) blood pressure; (3) heart rate; (4) blood sugar level; (5) blood oxygen level; (6) cholesterol level; (7) respiration rate; (8) hormone level; (9) galvanic skin response; (10) EMG; (11) EEG; (12) EOG; (13) body fat; (14) hydration level (15) activity level; (16) body position; (17)

UV radiation exposure; and (18) UV radiation absorption. BREM computer 18 may be configured to process bio-sensor data locally and to transfer/transmit processed or unprocessed sensor data to display 22 through communication link 27.

BRME computer 18 may be further configured to communicate with remote computer 36 through wired or wireless communication link(s), such as link 32, link 29 and link 38. Communication link 29 may be a typical Local Area Network (LAN) connection and hardware necessary to complete a communication connection between multiple devices. Such technology is well known by those of ordinary skill in the art. Remote computer 36 is connected to communication link 29 through communication link 38. Alternatively, BREM computer 18 may communicate directly with remote computer 36.

Remote computer 36 may be configured to store bio-sensor data and environmental-data in database 40. In addition, BREM computer 18 may receive processed bio-sensor data and environmental-data from remote computer 36 and transfer such data to display 22. Ideally, the components of BREM 12 may be reprogrammed and receive firmware updates and have features activated and features blocked using any properly configured computing device connected to communications link 29. Alternatively, BREM 12 may provide an interface port for directly connecting to external programming devices. Such interface ports are well known in the art. Exemplary interface ports include USB, infrared, serial, parallel, firewire or any other suitable port.

BREM computer 18 may be additionally configured to accumulate reference data. Exemplary reference data may include average values, peak values, minimum values as well as other statistical data such as standard deviations and data relating to the quintessential "average human". Such reference data would ideally be displayed along with environmental-data as well as real-time bio-sensor data for a particular body parameter such as heart rate. Thus, one purpose of presenting reference bio-reading data, environmental-data and real-time bio-reading data is to give the user of BREM 12 a reference by which current bio-sensor data may be compared thereby supplying added insight as to the meaning of the current bio-sensor data with the goal of preventing catastrophic health events before they happen.

To help explain the function of reference data, consider the following example relating to blood pressure. Assume a user is given a real-time blood pressure reading of 145/87. Such a blood pressure reading alone tells a user no more than his current blood pressure. Now suppose a user is presented with reference data long with his real-time blood pressure reading. For example, suppose display 22 presents the following to the user: (1) 1-year average blood pressure: 120/70; (2) 6-month average: 125/75; (3) 3-month average: 135/80; (4) 1-week average: 140/85; and (5) current reading: 145/87. Such data indicates an alarming trend in increased blood pressure readings over the last year and would likely motivate a user to seek a medical evaluation to determine the cause of such readings. Such a medical evaluation may be greatly enhanced if environmental-data recorded contemporaneously with such blood pressure data were available for evaluation.

One of ordinary skill in the art will recognize that displaying reference data in conjunction with current sensor data and environmental-data provides a powerful tool for physicians in treating patents. For example, many patents become apprehensive when visiting a doctor's office ("white coat syndrome"). Such apprehension may cause elevated blood-pressure levels each time a patient undergoes a medical exam. Under such conditions, and without access to both reference data and environmental-data, a physician may unnecessarily treat a patent for hypertension.

BREM computer 18 may accumulate reference data in a number of different ways in accordance with the present invention. Reference data may be body specific where such data is accumulated and/or processed locally by BREM computer 18 using bio-sensors 23. For example, a particular body's heart rate may be measured for a period of time and an average value calculated and stored for later use. BREM computer 18 may also transfer bio-sensor data to a remote computer, such as remote computer 36. The remote computer may process such data and calculate the required reference data and transfer such reference data back to BREM computer 18.

Reference data may also be "average human" reference data (previously described) relating to the average values of human bodies in general. BREM computer 18 may access a remote database containing "average human" reference data. Alternatively, reference data may be stored in a local memory.

Still referring to FIG. 1, one possible embodiment of electronic tag reader 20 for retrieving and/or receiving information from electronic tags associated with items in an environment is an RFID electronic tag scanner/reader (RFID STR). Electronic tag scanner 20 will be referred to as RFID STR 20 in the following discussion. Electronic tags are devices associated with items in an environment and configured to store and transmit information about their associated items. Such RFID STR and smart tag technology will be discussed more thoroughly later. The information contained in such electronic tags may be defined as environmental-data. For example, environmental-data may include any combination of: (1) EMI Code; (2) item identification number; (3) item model number; (4) warning code; (5) room code; (6) floor code; (7) building code; (8) vehicle code; (9) meal code; (10) nutrition code. For example, a "floor code" may simply be a number, such as 15, perhaps indicating a body is on the $15^{th}$ floor of a building.

Figure 3:
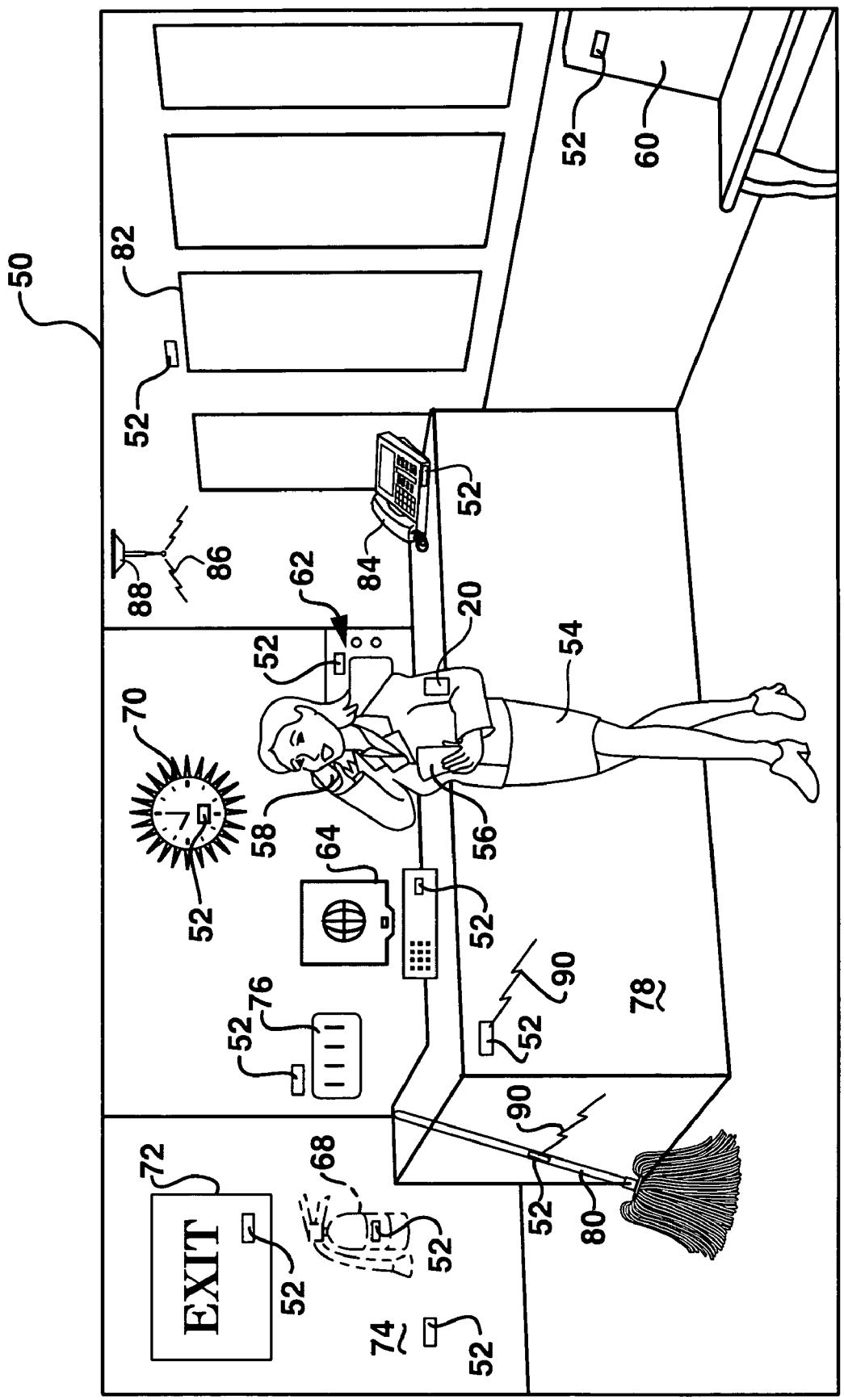
FIG. 3 is a graphic illustration of an exemplary environment containing items associated with electronic tags and an exemplary body with associated bio-reading and environment monitoring system.

RFID STR 20 may be of conventional design and may be configured to interrogate and retrieve information from electronic tags, such as RFID smart tags 52, shown in FIG. 3. RFID STR 20 may, for example, comprise an RF transmitter and receiver and an antenna to communicate with RFID transponders. RFID STR 20 may include a microprocessor and software programs for this purpose. Exemplary readers include Martics® Advanced Readers manufactured by Matrics, Inc. (Columbia, Md.), Alien Technology (Morgan Hill, Calif.), or Philips Semiconductor (Eindhoven, The Netherlands). Another example of an RFID STR device is an RFID reader manufactured by Antenova Ltd. (Cambridge, England) or Bancolini B30 handheld RFID Scanner manufactured by Bancolini (Bologna, Itally).

It should be appreciated that exemplary BREM 12 is intended to be a portable device worn by a body, such as human body. In such an application BREM 12 is ideally designed to be as convenient and comfortable to wear as possible. Such a design goal would typically necessitate a small, light weight design having minimal energy consumption. One design possibility would be to make RFID STR 20 a simple "listener" for receiving RFID smart tag transmissions. For such a configuration, BREM 12 would depend on remote (remote from BREM 12) RFID transmitters to supply the transmission signals (energy source) required to trigger RFID tag transmissions. Similarly, active RFID tags configured to periodically or continuously transmit a smart tag signal may be used.

Another low energy RFID STR 20 design may comprise an electronic device configured to first listen for RFID smart tag transmissions. If a RFID transmitter is in the area and transmitting a trigger signal, there may be no need for RFID STR 20 to transmit a trigger signal. If, however, no transmissions are detected within a predefined amount of time, RFID STR 20 may transmit a trigger signal to trigger transmissions from any RFID smart tag within range of the RFID STR 20 device. Additionally, RFID STR 20 may be configured to only transmit a trigger signal based on predefined transmit criteria. Such transmit criteria would ideally be user programmable and/or selectable and may include any combination of: (1) transmitting a trigger signal after a predefined amount of time elapses without receiving a valid electronic tag transmission; (2) transmitting a trigger signal periodically at set intervals; (3) transmitting a trigger signal periodically at random intervals; (4) transmitting a trigger signal upon manual request by a user; and (5) transmitting a trigger signal upon request transmitted by a remote computer.

In regard to transmit criteria (5) describe above, one exemplary remote computer is remote computer 36. Remote computer 36 may be configured, for example, to detect when environmental-data received by RFID STR 20 has been transmitted by only active RFID tags (described in more detail later). Under such conditions remote computer 36 may be configured to automatically request RFID STR 20 to transmit a trigger signal to determine if passive RFID tags are in the user's environment.

Alternatively, BREM 12 may have a manual mode of option where BREM 12 only transmits RFID Smart tag trigger signals upon a user request. For example, a user may issue a manual request to scan an environment by pushing a button associated with BREM 12. BREM 12 would respond by transmitting a RFID smart tag trigger signal and processing received RFID smart tag transmissions containing environmental-data. BREM 12 may additionally be configured with audio and/or video recording capabilities. Such a configuration may further include voice recognition technology. With such a BREM 12 configuration, a user may orally describe the environment or current activity. For example, a user may activate the BREM 12 audio record feature and state the following: "I am walking up a set of stairs". Such audio data would ideally be recorded in timed stamped memory (such as memory 17 or database 40) so that it may be accurately associated with environmental-data and bio-senor data taken contemporaneously with the audio recording.

RFID STR 20 may be further configured to communicate with display 22 and BREM computer 18 through wired or wireless communication links 21b and 21a respectively. Through such communication connections RFID STR 20 may send environmental-data to computer 18 and/or display 22. BREM computer 18 may process such environmental-data and may transmit processed and/or unprocessed environmental-data to remote computer 36. BREM computer 18 may also transmit any processed or unprocessed data to display 22.

Display 22 may comprise a number of display technologies. Exemplary display technologies may include any combination of: (a) a personal digital assistant; (b) a watch with an LCD display; (c) a watch with a segmented display; (d) an LCD display; (e) video-enabled glasses; (f) video-enabled goggles; (g) video-enabled helmets; (h) a video-enabled room; and (i) video-enabled transparent surface. One possible embodiment of a body wearable information processing terminal device is disclosed by Kita in U.S. Pat. No. 6,619,835 and such reference is incorporated herein by reference for all purposes. Exemplary virtual reality displays include systems by VR Jugger™, eGlass II™ Personal Viewer (heads-up display technology) manufactured by Virtual Vision, Inc., or AV-1, BV-3, SV-3, SV-9, EG-7 and CV-1 viewers manufactured by MicroOptical Corporation. Technology for displaying information on a windshield or other transparent surface in front of a user is disclosed by Stringfellow in U.S. Pat. No. 6,359,737 and such patent is hereby incorporated by reference for all purposes.

In one embodiment of the display 22, one or more screens in one or more rooms are provided as virtual reality display devices to provide data visualization of multiple physiological parameters (bio-readings) as well as environmental-data. A user may wear virtual reality goggles while exercising in a virtual reality "cave" having a plurality of walls capable of providing electronic images of bio-readings, reference data and environmental data. In another embodiment of the display 22, a heads-up data display may be provided that can present key biological parameters (bio-readings) such as pulse rate, average pulse rate, peak pulse rate, for example, as well as rich data environments such as virtual reality displays of three-dimensional or higher-dimensional representations of the information from the user. For example, statistics, charts, or 3-D data displays may be provided via displayed-enabled sunglasses, glasses, helmets, facemasks, goggles, driver's masks, and the like. Such technology is disclosed in U.S. Pat. No. 6,356,392 issued to Spitzer; U.S. Pat. No. 6,160,666 issued to Rallison et al.; U.S. Pat. No. 5,903,396 issued to Rallison; U.S. Pat. No. 6,157,291 issued to Kuenster et al.; U.S. Pat. No. 5,886,822 issued to Spitzer; U.S. Pat. No. 5,208,617 issued to Schwartz; and U.S. Pat. No. 4,867,551 issued to Perera and such patents are hereby incorporated by reference for all purposes.

BREM computer 18 may be further configured to monitor bio-sensor data and environmental-data and issue a BREM-alert when at least one of the monitored data sources meets predefined BREM-alert-criteria. A BREM-alert may be used to alert a remote party that a BREM 12 system has recorded certain predefined environmental-data and/or bio-senor data. A BREM-alert may be use for any reason but is ideally suited for providing emergency alerts. For example, elderly persons are prone to break bones in a fall. Should such a fall occur the injured person may not be able to request medical assistance. In additional, bio-readings alone may not be sufficient to indicate such an emergency situation exists. However, environment-data would likely indicate that a person's location has remained fixed for a prolonged period of time. For example, should a person's environmental-data indicate that the person is near an automobile in a garage outside a house, and such location has remained constant for a predefined period of time, such environment-data may suggest an injury. For such an example, the BREM-alert-criteria may be the amount of time a person's location remains substantially constant. Upon detecting such a condition, BREM computer 18 may be configured to call for emergency medical treatment and transmit the user's location to emergency personnel. Before transmitting a BREM-alert, however, BREM computer 18 would ideally notify the user that a BREM-alert transmission is pending and give the user an opportunity to cancel such BREM-alert. Such may be accomplished via a timed warning message.

BREM 12 may also be configured to issue warning messages when environmental-data is detected that meets predefined warning-criteria. Such a warning message may be issued to the BREM 12 user and/or to a remote party. For example, a person having a pacemaker may have a known list of electronic items that should be avoided. Similarly, a mop or a wet floor sign may indicate a wet and perhaps slippery floor condition. Even the most observant of people may not be aware of all items in a particular environment or may be distracted and fail to notice possible hazardous conditions. In addition, visually impaired people may not have the ability to visually inspect an environment for potentially hazardous conditions. BREM computer 18, Remote Computer 36 or some other computer associated with RFID STR 20 may be configured to compare environmental-data with a list of items that should be avoided or that may indicate a hazardous condition. When environmental-data is detected that indicates the user is near a hazardous item, RFID STR 20, a remote computer or BREM computer 18 may issue a warning message to the user. Such a warning message may be, for example, a beep, an audio voice message, a flashing light, a message displayed on display 22, a tactile signal such as a vibrating alarm, and a message printed out in Braille. Ideally, electronic tags, perhaps containing a warning code, would be associated with items such as microwave ovens, mops, wet floor signs, etc., by the BREM 12 user, the manufacture of the item, or persons in control of the environment, such as an employee of a hospital where the environment is a hospital.

Similarly, a user may be warned of a device that may affect the accuracy of bio-sensor data and wireless communications. Ideally, electronic tags programmed with an EMI (electromagnetic interference) code would be associated with items that are known to emit strong electronic fields. In the alternative, RFID STR 20, Remote Computer 36 and/or BREM computer 18 may compare environmental-data (such as model numbers) retrieved from smart tags associated with items in an environment with "stored data" in a memory (a list stored in a database associated with remote computer 36 is one example). Such "stored data" would ideally correspond to items known to radiate strong electronic magnetic fields. When environment-data is detected that indicates the existence of EMI hostile devices, the user could be warned to check BREM 12 for proper operation and/or BERM 12 could perform a self calibration and warn the user of improper operation.

BREM 12 may also be configured to communicate with treatment control systems. Exemplary treatment control systems may include pharmaceutical control systems (an insulin injection system is one example) and therapeutic control systems (air conditioning/heating systems or climate control systems, heating pad, localized cooling system, bed positioning control systems are examples). BREM 12 communicates with such control systems by generating treatment-signals. Treatment-signals are simply commands coded in electronic format that tell a control system what action to perform. Such treatment-signals may be generated by BREM computer 18 and transmitted to pharmaceutical treatment control 41 and/ or therapeutic treatment control 43 through a wired or wireless communication link 41a and 43a.

Such treatment-signals may be generated in response to bio-sensor data taken from a body being monitored as well as environmental-data describing the environment in which such bio-sensor data are being generated. Exemplary therapeutic treatments may include any combination of: (1) heating a body region, (2) cooling a body region, (3) modification of humidity levels, (4) adjustment of room temperature, (5) alteration of the position of a bed. One exemplary pharmaceutical treatment would be insulin injections from a portable drug delivery system associated with a body. Such insulin injections may be administered based on bio-sensor data that indicates, for example, that a body's glucose level has exceeded a predefined level. Portable drug delivery systems are well known by those of ordinary skill in the art.

One of ordinary skill in the art will realize that the each brand and type of treatment control system may have unique "command" sets, unique treatment-signal format requirements as well as different communication protocol requirements. Restated, each treatment control system is likely to have its own set of specialized commands that only it recognizes. First, a command set is simply a set of commands that tells a device what action to perform. Second, format requirements may be considered the "syntax" of a message (i.e. the way the commands need to be arranged). Third, communication protocol requirements are simply a set of detailed rules, sequences, message formats, and procedures that computer systems use and understand when exchanging data with each other.

For example, treatment-signal "inj 10 cc X;" includes four command codes in an exemplary syntax. For such exemplary treatment signal, command 1, "inj", means inject, command 2, "10", is the number 10, command 3, "cc", is a unit of measure (cubic centimeters in this example) and command 4, "X", is the substance to be injected (i.e. insulin). For such an example, "inj 10 cc X;" simply means "inject 10 cubic centimeters of substance X". The "syntax" requirement is to list: (a) the action first, (b) the amount second, (c) the units third and (d) the substance to be injected forth, with all commands separated by a space and the command string ending with a semicolon. The communications protocol may simply be the proper protocol for sending a message, such as the protocol for sending a wireless message using Wi-Fi technology or any other well known communication protocol.

Such treatment-signal formatting routines may be incorporated in a driver program. Generally speaking, a control system driver program is a device specific program that acts like a translator between the device and other programs that use the device. As noted above, each treatment system controller is likely to have its own set of specialized commands that only it recognizes. To allow BREM 12 to use generic commands, a driver program may be used that accepts generic commands from a BREM program and then translates them into specialized commands for the treatment control system. Such a program would ideally be automatically uploaded into a BREM 12 computer (using environmental-data as described below) and used to format and transmit treatment-signals.

BREM 12 is ideally configured to automatically determine (hereafter referred to as auto-configuration) (1) the type and/ or brand of treatment control system(s) to be used and (2) the command, syntax and protocol requirements (or driver file) needed to communicated with such treatment control system(s). The value of the auto-configuration function may be best explained by way of example. Consider a standard universal infra-red television remote control. Anyone who has had the opportunity to program a universal remote control to operate a particular television will appreciate the tedious and sometimes complex nature of such an exercise. If the universal remote control is configured incorrectly, an incorrectly formatted infra-red signal is sent to the television resulting in improper operation. For such an example, the TV may not operate or may jump to the wrong channel. Similarly, should a treatment control system receive improperly formatted treatment-signals (control signals), the treatment control system may not work, or perhaps even worse, may provide the wrong treatment.

The BREM computer 18 may communicate with an external control system through communication link 29 and request control system identification information. Alternatively, the BREM 12 auto-configuration function may be accomplished using environmental-data retrieved by RFID STR 20. RFID STR 20 may be configured to retrieve product information from electronic tags associated with pharmaceutical treatment control 41 and/or therapeutic treatment control 43 to obtain, for example, model number information. BREM computer 18 could then use such identification information to request auto-configuration information from a remote computer. Such auto-configuration information may be in the form of a treatment-system-controller driver program. Alternatively, BREM computer 18 could download/transfer information from a local memory, such as an EEPROM memory 17, which stores auto-configuration information for a plurality of control systems. With such information, BREM computer 18 can perform an automatic configuration function that assures properly formatted treatment-signals.

For example, assume that BREM computer 18, using RFID STR 20, retrieves the model number for bed controller X near the body associated with BREM 12. BREM computer 18 may access database 40 and use such model number information to retrieve and install a bed controller X driver program. When BREM computer 18 determines that the bed position should be changed, BREM computer 18 may use such driver program to format treatment-signals that are transmitted to bed controller X.

Referring now to FIG. 2, BREM/BRM systems may also be used to monitor a plurality of bodies. BRM systems are systems that do not include an electronic tag scanning device (although only BREM systems are depicted in FIG. 2). BREM/BRM systems may be associated, for example, with members of a football team. Such functionality provides coaches as well as fans with the ability to track the physical condition of players during games. During a game, fans and coaches may find the fatigue level, as indicated by heart rate, of particular importance. On a hot summer day, the hydration level of a player may be of particular importance to a coach. To facilitate remote access to a plurality of BREM/BRM systems, a networking system, such as a local area network (LAN) shown in FIG. 2 may be utilized. In such an exemplary embodiment, BREM/BRM system 11 may incorporate a TCP/IP protocol suite and an HTTP (HyperText Transfer Protocol) server to provide two-way access to the BREM/BRM system data. Such TCP/IP protocols and HTTP server technology are well known in the art.

For such an embodiment, the BREM systems 14 and 16 may include an HTTP server and a TCP/IP protocol stack. Alternatively, an HTTP server and a TCP/IP protocol stack may be included in LAN computer 102. Such a configuration would eliminate the need to include an HTTP server in each BREM system. Communication link 29 may comprise a gateway 100 which enables continuous remote access to BREM/BRM system devices. Alternatively, such gateway may be incorporated in LAN computer 102. A gateway is generally defined as an electronic device that connects two otherwise incompatible systems; however, a gateway may simply be a connection between two compatible systems.

The TCP/IP protocol suite may be incorporated into gateway 100 serving multiple BREM/BRM systems via a wired or wireless two-way network. Gateway 100 may also incorporate an HTTP server for accessing data from multiple BREM/BRM devices and for transmission of data to individual BREM/BRM devices.

In the above described TCP/IP enabled BREM and BRM systems, communications link 38a provides access to a first network operating in accordance with a predetermined protocol (TCP/IP is one example). A plurality of BREM and/or BRM devices may comprise a second network, such as a LAN. In FIG. 2, the second network comprises LAN Central Computer 102 is connected to a plurality of BREM devices, BREM 14 and BREM 16. A gateway 100 operatively couples the first network to the second network. Finally, an HTTP server is embedded in either the gateway 100, LAN Central Computer 102 or the plurality of BREM/BRM devices facilitating the transfer of data between the two networks. Additionally, gateway 100 may be incorporated into LAN Central Computer 102.

Such technology is fully disclosed by Ardalan et al. in U.S. Pat. No. 6,363,057 for use in a system for communicating with electricity meters, which is hereby incorporated by reference for all purposes.

With such a configuration, one of ordinary skill in the art will appreciate that individual BREM/BRM devices or groups of BREM/BRM devices may be accessed as if the devices were a web site and their information could be displayed on a web browser. Remote computer 36 may be, for example, a computer owned by a fan watching a football game on television where remote computer 36 is configured to display bio-reading information for selected players in the game. Additionally, using such a BREM system, a fan could request RFID STR 20 to scan a player to determine the type and brand of equipment the player is using. Bio-reading data and environmental-data could be displayed on a television screen viewable by anyone watching the game.

Referring now to FIG. 3, exemplary environment 50 is shown. In exemplary environment 50, electronic tags 52 are shown associated with items in the environment. In the present configuration, BREM 12 is a portable device associated with body 54. Note that the exemplary BREM 12 embodiment of the present invention comprises RFID STR 20, BREM computer 18 and display 22 as separate components. It should be appreciated that the following discussion may be equally applicable to integrated systems such as BREM 14 and BREM 16. RFID STR 20 may be in communication with BREM computer 18 (not shown) through a wired or wireless communication link 21a (FIG. 1) using communication technologies such as Bluetooth and Wi-Fi. Such wireless communications technologies are well known in the art. RFID STR 20 may be incorporated within a personal digital assistant 56 (PDA), a cell phone 58 or some other portable computing device.

The electronic tags 52 may be attached directly to items as illustrated in FIG. 2. In this embodiment, the electronic tag 52 may be, for example, adhesive backed labels or tags that are attached directly to the items. Such electronic tag 52 may be attached to the items at the place of manufacturer, by a retailer that sells the items, a user, persons in control of the environment or some other entity.

The product identification information stored in the electronic tag 52 is not to be limited in scope, and may include, for example, information identifying the type of product, brand name of product, manufacturer of the product, etc. The type of product information stored in electronic tag 52 should be adequate to correlate with various manners of listing items. Items and associated electronic tags 52 depicted in exemplary environment 50 include chair 60, microwave oven 62, computer 64, fire extinguisher 68, clock 70, exit sign 72, wall 74, light switch 76, desk 78, mop 80, window 82 and phone 84. The information stored in electronic tag 52 associated with microwave oven 62, for example, may include an EMI code as well as a warning code which may be used to warn body 54 of possible interference with electronic devices associated with body 54. The information stored in electronic tag 52 associated with mop 80 may include a warning code that may be used to warn body 54 of a possible wet floor. The electronic tag 52 associated with fire extinguisher 68 may include location information informing body 54 that fire extinguisher 68 hangs on the other side of wall 74. The electronic tag 52 associated with exit sign 72 may be used to inform body 54 of a way out of a building, which may be particularly important in a smoke filled or poorly lit environment. Knowing the location of light switch 76 may be useful when the lights in exemplary environment 50 are not on and the environment is dark. Knowing the location of all the items in exemplary environment 50 may be of great assistance to a visually impaired body. Indeed, it should be clear to one of ordinary skill in the art that exemplary BREM 12 according to aspects of the present invention gives even the visually impaired body the ability to see in the dark, peer around corners and look through walls (figuratively speaking).

Exemplary electronic tag and electronic tag reader/scanner technology are now discussed in more detail. One smart tag 52 technology that may be used is RFID smart tags. With conventional RFID "smart" systems, the smart tags 52 are passive devices. Referring to FIG. 3, RFID STR 20 may emit a trigger excitation signal 86 (not shown) that is received by internal antenna in a smart tag 52. Alternatively, trigger excitation signal 86 may be generated by transmitter 88. This excitation signal 86 causes the smart tag 52 to generate and transmit signal 90, an electromagnetic pulse of coded digital data containing the product identification information. The coded signal 90 is received by the RFID STR 20, decoded and perhaps transmitted to BREM computer 18, remote computer 36 and/or display 22 in any number of ways.

RFID smart tag technology is known and understood by those skilled in the art, and a detailed explanation thereof is not necessary for purposes of describing the method and system according to the present invention. Generally, conductive or passive smart tags 52 consist of silicon or other semiconductors, a coiled, etched, or stamped antenna, a capacitor, and a substrate on which the components are mounted or embedded. A protective covering is typically used to encapsulate and seal the substrate. Inductive or passive smart tags have been introduced by Motorola under the name "BiStatix." A detailed description of the BiStatix device may be found in U.S. Pat. No. 6,259,367 B1, incorporated herein by reference in its entirety for all purposes. Another commercial source of suitable smart tags is Alien Technology Corporation of Morgan Hill, Calif., under the technology name FSA (Fluidic Self-Assembly). With the FSA process, tiny semiconductor devices are assembled into rolls of flexible plastic. The resulting "smart" substrate can be attached or embedded in a variety of surfaces. The smart tag technology under development at the Auto-ID Center at Massachusetts Institute of Technology (Cambridge, Mass.) can also be used within the scope of the present invention. Further information on smart tags and related technology is disclosed in U.S. Pat. No. 6,451,154, "RFID Manufacturing Concepts," issued Sep. 17, 2002 to Grabau et al.; U.S. Pat. No. 6,354,493, "System and Method for Finding a Specific RFID Tagged Article Located in a Plurality of RFID Tagged Articles," issued Mar. 12, 2002 to Mon; PCT publication WO 02/48955, published Jun. 20, 2002; U.S. Pat. No. 6,362,738, "Reader for Use in a Radio Frequency Identification System and Method," issued Mar. 26, 2002 to Vega; D. McFarlane, "Auto-ID Based Control," White Paper for the Auto-ID Centre Institute for Manufacturing, University of Cambridge, Cambridge, United Kingdom, Feb. 1, 2002, available at www.autoidcenter.org/research/CAM-AUTOID-WH-004.pdf; and Chien Yaw Wong, "Integration of Auto-ID Tagging System with Holonic Manufacturing Systems," White Paper for the Auto-ID Centre Institute for Manufacturing, University of Cambridge, Cambridge, United Kingdom, September 2001, available at www.autoid-center.org/research/CAM-WH-001.pdf. Such references are hereby incorporated herein by reference in their entirety for all allowed purposes.

Other RFID technologies believed to be of value for the present invention include those produced by Microchip Technologies (Chandler, Ariz.), which provides remote read-write chips at several frequencies. Also of potential value are the I*CODE chips and readers of Philips Semiconductor (Eindhoven, The Netherlands), which, in one embodiment, are said to include 384 bit configurable read/write memory with 64 bits for a unique serial number (e.g., an electronic product code). Sokymat (Lausanne, Switzerland) markets the PIC-COLO read-only RFID disc tag which transmits data to a reader station by an AM radio signal. The tag is said to have 64 bits of data that can be programmed during manufacture by laser fusing of polysilicon links in order to store a unique code on each tag.

Texas Instruments (Dallas, Tex.) offers RFID technology as part of Texas Instruments RFID (TI*RFID™) Systems, formerly known as the TIRIS™ system (Texas Instruments Registration and Identification System), which is used to track and identify various assets using devices such as the TI Tag It™ chip.

Gemplus (Gemenos, France) provides smart tags (sometimes called "smart labels") and smart cards employing RFID technology, which may be used as smart tags. They also market interfaces, antennas, scanners and software that can be adapted for use with smart tags.

Nedap (Groenlo, The Netherlands) provides smart cards and a 13.56 MHz smart tag using RFID technology with 512 bits of read-write memory and a range of about 120 cm. It is claimed that about 20 such tags per second can be read successfully by a scanner.

Checkpoint Systems Inc. (Miami, Fla.) offers a smart tag with WORM technology (write once, read many). One example is the MCRF355 chip, described more fully at www.idsystems.com/reader/1999_05/join0599.htm.

PDA-like reader systems and other portable readers for RFID technology are marketed by Omron Company (Tokyo, Japan), such as the Model V700 or V720 series.

High frequency bands can be used in RFID technology, such as bands between 300 MHz and 10 GHz. SCS Corporation (Rancho Bernardo, Calif.), for example, markets smart tag technology at 2.45 GHz. Ultra-wide band technology can also be adapted for RFID systems.

A related technology within the scope of the present invention is Surface Acoustic Wave (SAW) technology. For example, InfoRay (Cambridge, Mass.) markets a passive smart tag that is said to achieve long ranges (up to 30 meters) using a Surface Acoustic Wave (SAW) device on a chip coupled with an antenna. The SAW device converts a radio signal to an acoustic wave, modulates it with an ID code, then transforms it to another radio signal that is emitted by the smart tag and read by a scanner. The ID code of the smart tag is extracted from the radio signal. The scanner is said to compare the spectral content of the signal with a database of signatures to derive the ID code. This method enables a read range of up to 30 m (typical 10-20 m). The system can operate in the 915 MHz band and 2.45 GHz band. RFSAW, Inc. (Dallas, Tex.) also provides minute Surface Acoustic Wave (SAW) RFID devices that can be used within the scope of the present invention.

The antenna embedded within the smart tags 52 is generally one component of the device, though it is recognized that alternatives to antennas may exist in some applications. For example, for some metallic objects, the smart tag need not comprise an antenna but the metallic object itself can serve as the antenna. The excitation signal 86 from the RFID STR 52 can be received by the antenna to "activate" the smart tag. The received excitation signal 86 is the power source for the smart tag 52 and results in the generation of the electromagnetic pulse containing the coded product/item identification information signal 90. A detailed description of RFID smart tag antennas may be found in U.S. Pat. No. 6,320,556 B1, incorporated herein by reference for all purposes.

In an alternate embodiment, the smart tags 52 may be active devices. In this configuration, the smart tag 52 includes active transceiving circuitry that has the capability to selectively respond to coded request signals transmitted by an RFID STR 52. The active smart tag 52 may include the capability to delete its fixed code and receive new or additional information beyond the information contained in its fixed code. An active smart tag 52 requires an internal power supply, such as a micro-battery, thin film battery, or the like. Active tags 52 may be desired in the scenarios wherein the tags 52 are mounted at storage locations of particular products. In this way, as different products are stored at the respective locations, the smart tags 52 can be programmed accordingly.

Figure 4:
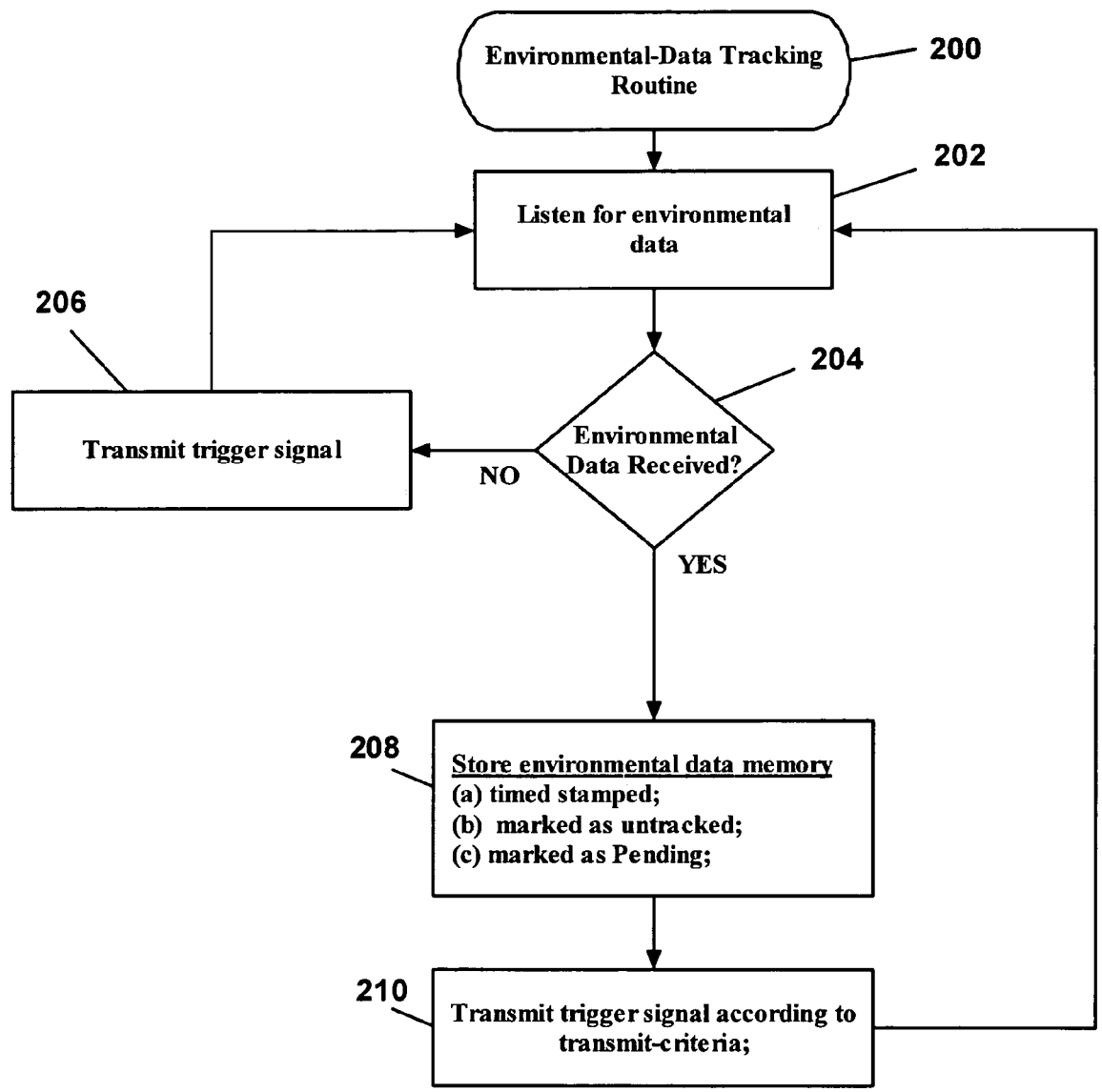
FIG. 4 is a logical flow chart of an exemplary Environmental-data routine according to the invention.

Examples of methodologies for using exemplary BREM systems 12, 14 and 16 are depicted in high level block diagrams present in FIG. 4 through FIG. 8. FIG. 4 depicts exemplary logic for tracking environmental-data. Such an environmental-data tracking routine is ideally implemented in software executed by BREM computer 18. It should be appreciated, however, that any computer with access to communications link 29 may be the computer executing the environmental-data tracking routine and hereafter such computer will simply be referred to as the "central computer". It should also be noted that the general goal of tracking environmental-data is to provide a means for determining the effects a body's environment has on the generation of such body's bio-readings as determined using bio-sensors. Thus, environmental-data and bio-sensor data should be stored in a manner that allows correlation in time (time synchronization) between the two sets of data. Thus, environmental-data and bio-sensor data (bio-reading data) are ideally stored in a memory, such as memory 17, so that the time such data was generated can be ascertained. One exemplary method is to store such data in memory along with the time such data was recorded.

FIG. 4 depicts a high level block diagram describing an exemplary Environmental-data Tracking routine. Step 200 marks the entry point into such routine. At step 202, the central computer listens for electronic tag transmissions to determine if an electronic tag trigger signal, such as trigger signal 86 (FIG. 2), should be transmitted by RFID STR 20 associated with body 54. As previously noted, if a trigger signal has already been transmitted by transmitter 88, for example, or if active electronic tags are being used, there may be no need for RFID STR 20 to waste energy transmitting an additional trigger signal. Such a condition can be determined by first listening for electronic tag transmissions. If at step 204 no electronic tag transmissions are detected, program control passes to step 206 and an electronic tag trigger signal is be transmitted. It should be appreciated that such transmission may be delayed by a timing routine to prevent continuous transmissions or too frequent transmissions.

If, however, at step 204 environmental data has been received, program control passes to step 208. At step 208 such data is stored in a timed stamped memory, marked as "untracked" and marked as "pending". Ideally, a non-volatile memory such as EEPROM or a hard drive type memory is used to store such data. A volatile memory may also be used to store such data. The term "time-stamped memory" simply refers to some method of marking stored environmental-data so that the time the item (associated with such data) was encountered may be determined. The term "untracked" signifies that the environmental-data has not yet been determined to be worthy of being tracked. The term "pending" signifies that the environmental-data has not been evaluated to determine if such environmental-data classification should be changed to "track" (described later).

Next, at step 210, the central computer determines if a trigger signal should be transmitted based on predefined transmit-criteria. Exemplary transmit-criteria may include any combination of: (1) periodically at set intervals; (2) periodically at random intervals; (3) upon manual request by a user; and (4) upon request automatically generated by a computer. For example, if the central computer determines that all the received environmental-data has been transmitted by active electronic tags, the central computer may request RFID STR 20 to transmit a trigger signal to check for passive tags that may be present. After step 210, program control loops back to step 202.

Figure 5:
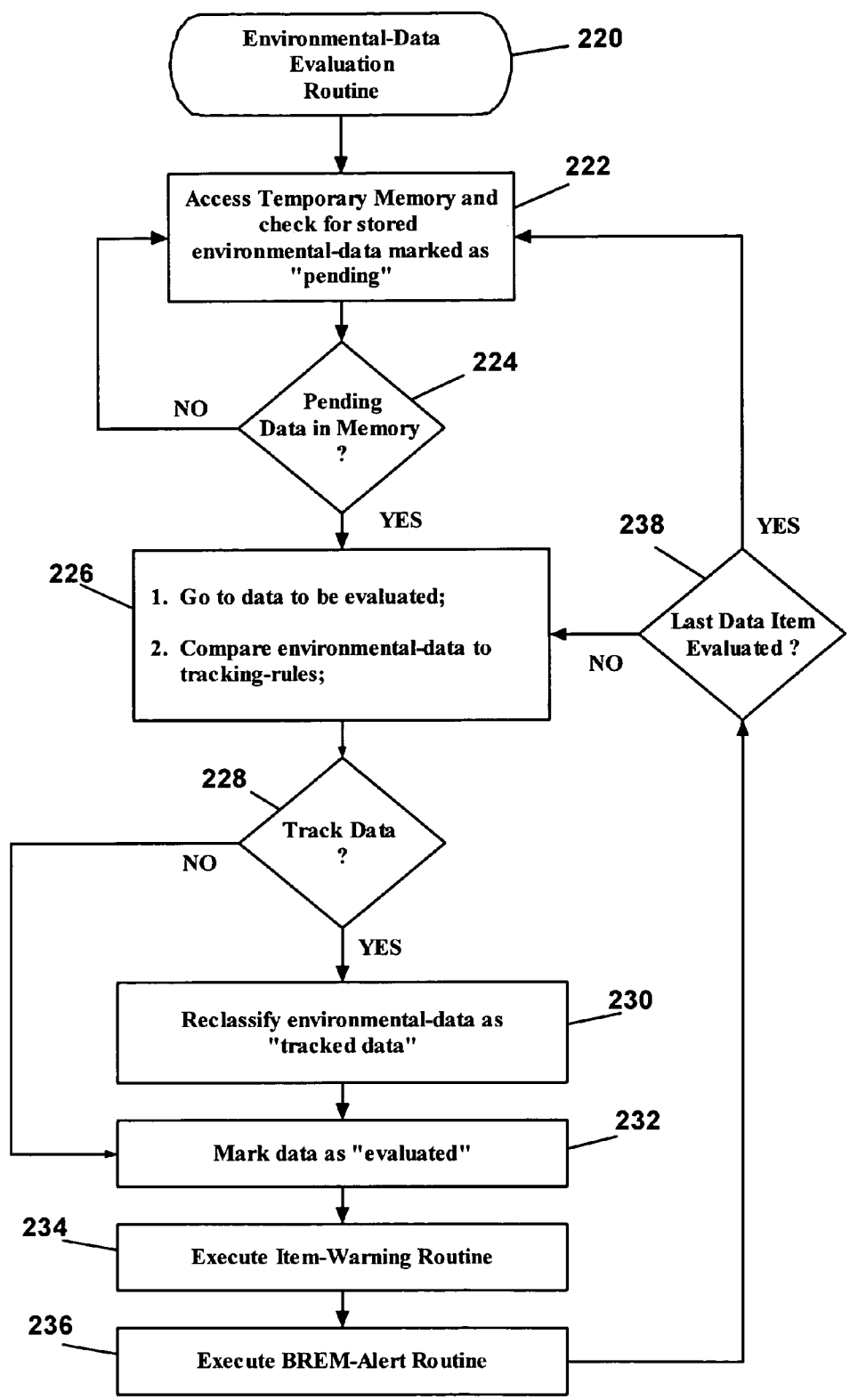
FIG. 5 is a logical flow chart of an exemplary Environmental-data Evaluation routine according to the invention.

FIG. 5 presents an exemplary Environmental-data Evaluation routine where step 220 marks entry into such a routine. At step 222, the central computer accesses environmental-data memory to check for stored environmental-data marked as pending. It should be appreciated that any computer with access to communications link 29 may be the computer executing environmental-data evaluation routine 220. Alternatively, the Environmental-data Evaluation routine may be incorporated into the Environmental-Data Tracking routine. As noted above, pending environmental-data has not yet been evaluated to determine if such data is to be tracked. If at step 224 the central computer determines that no pending environmental-data exists in memory, program control loops back to step 222. If, however, at step 224 the central computer determines that pending environmental-data is stored in memory, program control passes to step 226 where the next environmental-data to be evaluated is compared to predefined tracking-rules.

Tracking-rules are simply predefined rules that are used by the central computer to determine if environmental-data should be tracked. For example, while shopping in a grocery store body 54 using BREM 12 may pass near 50 jar of jelly, all having electronic tags and transmitting environmental-data. It is unlikely that body 54 would need to track each jar of jelly. Thus, a tracking-rule (in words, not code) may be as follows: "If environmental data received for an item is substantially identical to environmental data already recorded in the current environment over a predefined interval of time, only track 1 such item and maintain a counter value." Using such a rule, for the above example, the environmental-data for the first jelly item would be tracked and a counter value would be maintained indicating how many jelly items were present. Alternatively, a user may wish to record the detection of only one jar of jelly (no counter) or simply ignore all such data.

One of ordinary skill in the art will recognize that such tracking-rules are likely to be quite diverse and body/user dependent, however, there will likely be a set of default rules for tracking items. For example, the central computer may be configured to always track environmental-data relating to the location of exit doors, safety items such as fire extinguishers and known dangerous items such as firearms.

If at step 228 the environmental-data being evaluated is to be tracked, program control passes to step 230 where such environmental-data is reclassified as "tracked data" after which program control passes to step 232. If, however, at step 228 the central computer determines that the environmental-data being evaluated is not to be tracked, program control skips to step 232. At step 232, the environmental-data is marked as having been evaluated. Next, program control passes to step 234 where an exemplary Item-Warning routine (described below) is executed. When program control returns from the Item-warning routine, an exemplary BREM-alert routine (described below) is executed. When program control returns from the BREM-alert routine, program control passes to step 238 where the central computer determines if any more environmental-data is pending evaluation. If pending environmental-data is located, program control passes back to step 226. Otherwise, program control passes back to step 222.

It should be appreciated that, ideally, tracked and untracked environmental-data will be stored in a memory for later review. One way in which tracked environmental-data differs from untracked data is that tracked environmental-data is intended to be presented along with bio-sensor data upon user request (or automatically presented). As noted previously, such data may be presented to a user in any number of ways. Tracked and untracked environmental-data may be compressed and archived as needed using well known programs designed for such functions. Notably, a review of untracked environmental-data may inspire the creation of new rules based on environmental-data/bio-sensor data relationships not previously appreciated. Such a review of untracked environmental-data may useful, for example, in searching for an explanation as to the cause of unusual bio-sensor data that has been recorded. As an alternative, particularly in systems with limited memory, untracked environmental-data may simply be discarded.

Figure 6:
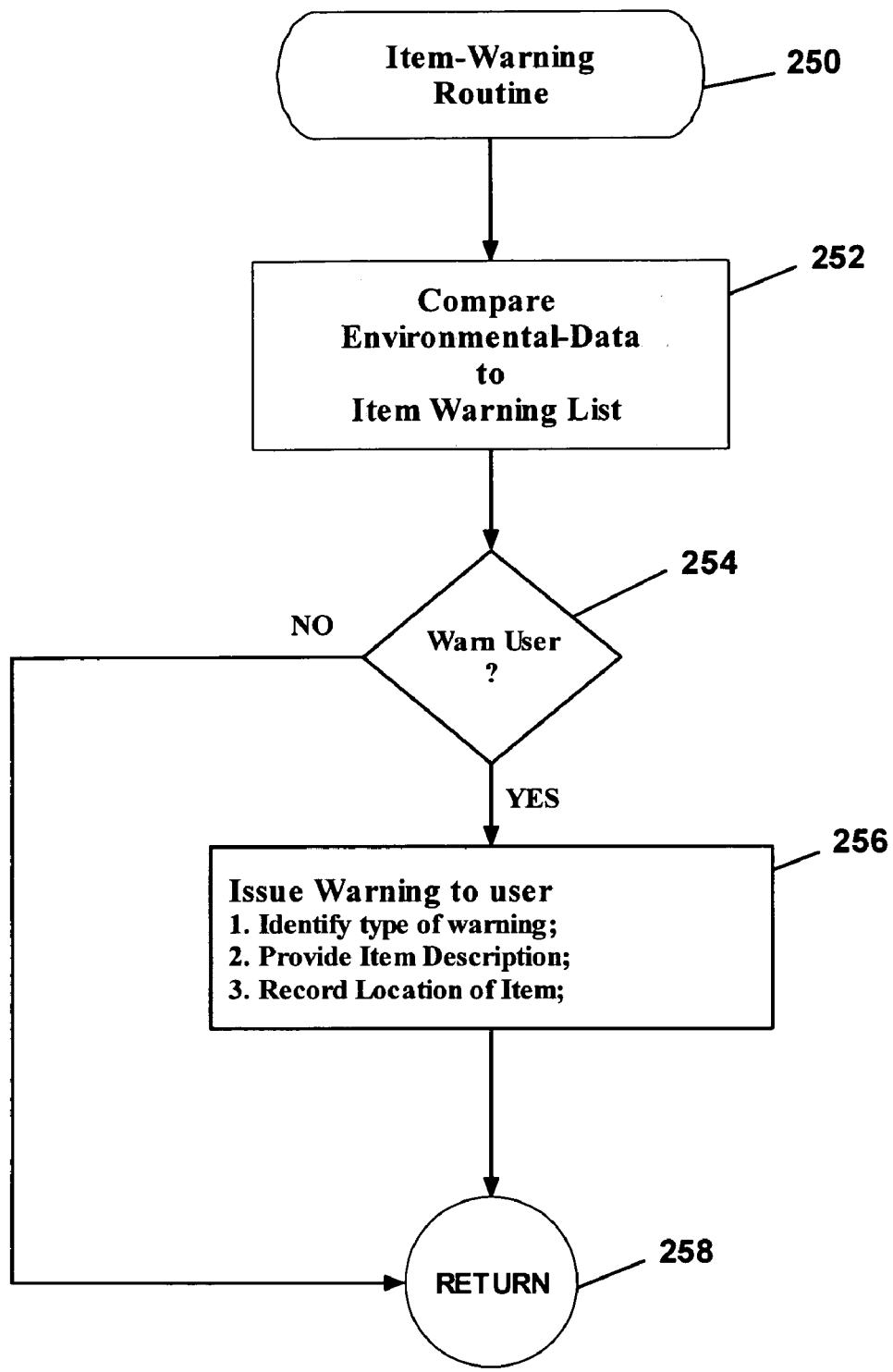
FIG. 6 is a logical flow chart of an exemplary Item-Warning routine according to the invention.

Attention is now directed to FIG. 6 and the exemplary Item-Warning routine. The purpose of the Item-Warning routine is to warn a BREM 12 user of a possible dangerous item or hazardous condition detected in the user's environment. Such items may be electronic devices that generate strong electromagnetic fields that can interfere with the proper operation of BREM 12 or other electronic items associated with body 54 (such as a pacemaker). For example, warnings may be issued to warn a user of items as simple as a mop, which may indicate the possibility of a wet floor. A BREM 12 user may be issued a warning where such warning comprises a voice/text message consistent with the information on a warning sign. Such signs are well known and commonly used to provide a visual notification of a potentially dangerous environmental condition. Examples of such signs include wet floor, hot surface and slippery surface, watch your head, watch your step, high voltage, etc. Similarly, warnings may be issued that are consistent with informative type signs, such as wet paint, do not touch, Library, Bathroom or no smoking.

Step 250 marks entry into an exemplary Item-Warning routine. At step 252, environmental-data is compared to warning-criteria. If the environmental-data associated with an item in the user's environment indicates that a user should be warned that such an item is in the user's environment, a warning message is issued to the user. Warning-criteria may be any suitable criteria that the central computer may use to determine if a user should be warned of an environmental item or situation. Thus, warning-criteria may simply be a list of item model numbers or general item descriptions (i.e. microwave). The warning message may be formatted in any number of ways and may include any combination of the following: (1) a description of the item; (2) the location of the item; and (3) a description of the warning (warning message). Exemplary warning messages may include any combination of: (1) a warning specific beep; (2) an audio voice message; (3) a flashing light; (3) a message displayed on a display; and (4) a message printed in Braille. Also, the warning-criteria and the location of the item that caused the warning to be issued may be recorded for future reference. Storing previous warnings and information describing the items that caused such warnings and the item's location provides for the ability to warn a user of a possibly dangerous location before the user enters such location. It should be appreciated that warnings my also be transmitted to a remote computer.

Figure 7:
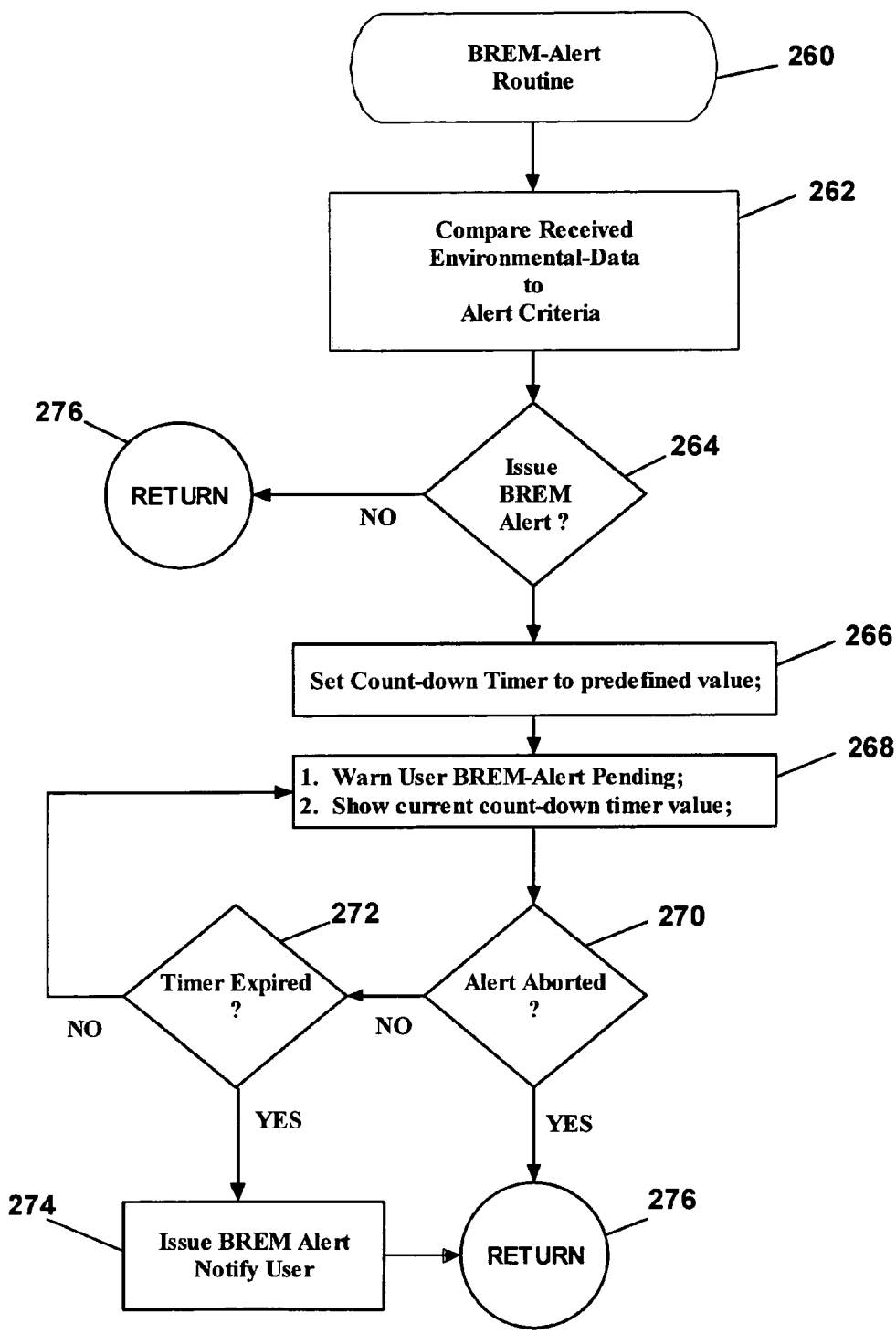
FIG. 7 is a logical flow chart of an exemplary BREM-alert routine according to the invention.

Referring now to FIG. 7, an exemplary BREM-alert routine is illustrated where step 260 marks the entry into the routine. Generally speaking, a BREM-alert is a transmission sent to a remote party. Such transmission may indicate, for example, an emergency condition exists that threatens the well being of a body associated with BREM 12. At step 262, environmental-data is compared to BREM-alert criteria. BREM-alert criteria are any suitable criteria a computer may use to determine if an alert condition exists, particularly emergency conditions. For example, if a person is knocked out, passes out or otherwise becomes incapacitated, such a person's environmental-data will remain relatively constant (depending on the environment). Thus, exemplary BREM-alert criteria may include the following: "If environmental-data remains 95% constant in a non-exempt location, initiate a BREM-alert". An example of an exempt location might be a couch in a person's living room. At step 264 the central computer determines if the current environment-data meets any BREM-alert criteria in a predefined BREM-alert criteria list. If the central computer determines that no alert condition exists, program control returns to the calling routine (Environmental-data Evaluation Routine for this embodiment). If, however, the central computer determines that a BREM-alert should be issued, program control is transferred to step 266. At step 266, a count down timer is initialized to a predefined value, such as 60 seconds. Program control then continues to step 268 where the user is warned of a pending BREM-alert transmission, the countdown timer value is presented and the user is given the opportunity to cancel the BREM-alert transmission during the timed period. Such information may be displayed, for example, on displayed 22. At step 270, the central computer determines if the BREM-alert has been aborted, and if so, program control returns to the calling routine. If, however, the BREM-alert has not been aborted, program control transfers to step 272 and the central computer checks to see if the countdown timer has expired. If the countdown timer has not expired, program control returns to step 268 and the BREM-alert notification information presented to the user may be updated (for example, updating the countdown timer value). If, however, the countdown timer value has expired, program control jumps to step 274 and a BREM-alert is transmitted to the appropriated entity (i.e. a fire department, police department and/or emergency medical service personnel, a remote computer, etc.). The user may also be notified that the BREM-alert transmission has been transmitted and display on display 22 the status of any response. Such a response may be a message indicating that the police have been notified and the estimated time of arrival is 10 minutes.

Figure 8:
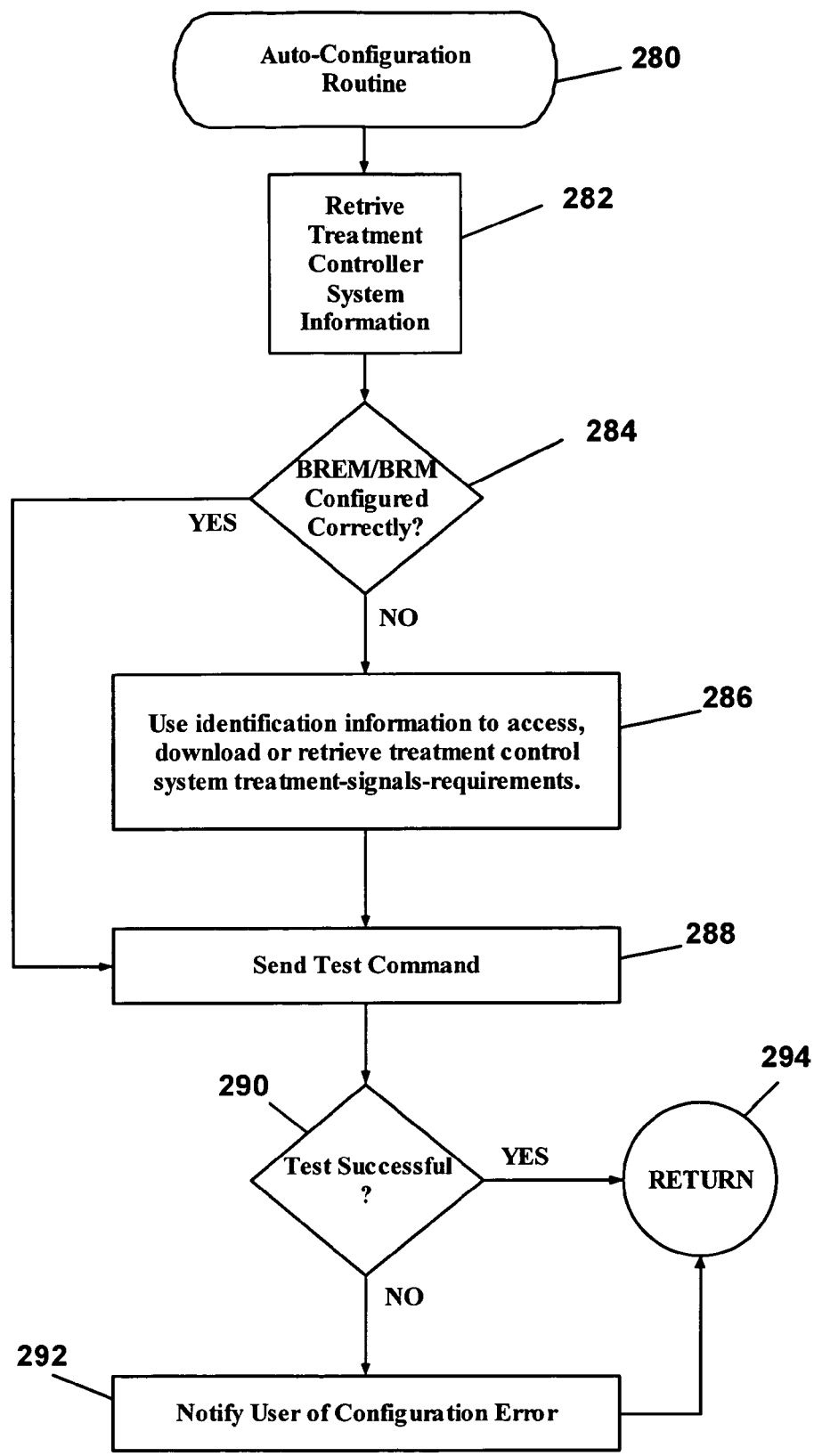
FIG. 8 is a logical flow chart of an exemplary Auto-Configuration routine according to the invention.

Attention now is directed to FIG. 8 which depicts an exemplary Auto-Configuration routine. The purpose of the auto-configuration routine is to automatically configure a BREM 12 system to generated properly formatted treatment-signals required to accurately communicate with a treatment controller, such as a pharmaceutical treatment control system (i.e. drug delivery system) or a therapeutic control system (such as air conditioning systems, bed positioning systems, etc.). As previously noted, treatment-signals typically must be precisely formatted to communicate accurately with a treatment control system. Treatment-signal formatting criteria may be provided in the form of a treatment-controller driver file. For BREM 12 to auto-configure its treatment-signal generation means, BREM 12 requires information (identification information would be particularly useful) about the type of treatment-controllers located in the BREM 12 user's environment. The auto-configuration routine first determines the treatment controllers present in a user's environment (perhaps using environmental-data retrieved by RFID STR 20). With such information, the auto-configuration routine automatically retrieves the treatment-controller driver file(s) necessary to format treatment-signals to correctly communicate and control a treatment control system.

Step 280 marks entry into the auto-configuration routine. At step 282, the central computer retrieves treatment-control-system-information. Such treatment-control-system-information may include the necessary treatment-signal criteria requirements or may simply be treatment-controller identification information. The central computer may retrieve treatment-control-system-information using an electronic tag scanning device, such as RFID STR 20. Alternatively, the central computer may communicate directly with the treatment-controller using wireless communication technology such as Wi-Fi. At step 284 the central computer compares the retrieved treatment-control-system-information with the current treatment-controller information for which BREM 12 had been previously configured. If the central computer determines the received treatment-control-system-information is different from the current treatment-controller information, the central computer obtains new treatment-signal criteria and reconfigures BREM 12 to use the new treatment-signal criteria (step 286). The central computer may obtain new treatment-signal criteria by accessing a remote computer or a local memory associated with BREM 12. One exemplary local memory would be EEPROM memory.

If, however, at step 284, the received treatment-control-system-information is the same as the current treatment-controller information, program control simply jumps to step 288. At step 288 a test command may be sent to the controller to help verify proper BREM 12 configuration. Such a step is optional but recommended. At step 290 the central computer determines if the test command was successful (automatically if two-way communication is possible). If the command was not successful, program control passes to step 292 and the user is warned of a configuration error. Otherwise, program control simply returns to the calling routine.

While the present subject matter has been described in detail with respect to specific embodiments thereof, it will be appreciated that those skilled in the art, upon attaining an understanding of the foregoing may readily adapt the present technology for alterations to, variations of, and equivalents to such embodiments. Accordingly, the scope of the present disclosure is by way of example rather than by way of limitation, and the subject disclosure does not preclude inclusion of such modifications, variations, and/or additions to the present subject matter as would be readily apparent to one of ordinary skill in the art.

It should also be appreciated that the system and method according to the invention are not limited to any particular type of commercial or market scenario, but have application wherever consumer goods or products are typically purchased in accordance with a predefined or predetermined list of such products.

What is claimed is:

1. A body and environment monitoring system comprising:
   at least one bio-sensor associated with a body and configured to generate sensor-data related to at least one body-parameter;
   a first computer in communication with said at least one bio-sensor and configured to retrieve sensor-data from said at least one bio-sensor;
   at least one electronic tag scanning device configured to retrieve environmental-data stored in electronic tags associated with items in an environment wherein said at least one electronic tag scanning device is one of (a) adapted to be mounted on said body, (b) adapted to be attached to said body and (c) adapted to be carried by said body, said electronic tags remaining with their respective associated item within the environment such that said electronic tag scanning device retrieves the environmental-data when the monitored body comes within a predetermined range of said electronic tags, said stored environmental data relating to a characteristic of the associated item that is relevant to interpretation of the bio-sensor data; and
   memory for storing at least one of said sensor-data and said environmental-data and wherein said memory is at least one of a volatile memory and a non-volatile memory.

2. A body and environment monitoring system as in claim 1, wherein said environmental-data is at least one member from the group consisting of: (1) EMI Code; (2) item identification number; (3) item model number; (4) warning code; (5) room code; (6) floor code; (7) building code; (8) vehicle code; (9) meal code and (10) nutrition code.

3. A body and environment monitoring system as in claim 1, wherein said first computer is configured to generate at least one of therapeutic treatment-signals and pharmaceutical treatment-signals when a monitored body-parameter meets predefined treatment-criteria.

4. A body and environment monitoring system as in claim 3,
   wherein said at least one electronic tag scanning device is further configured to communicate with said first computer and to transfer at least part of said environmental-data to said first computer; and
   wherein said first computer is further configured to automatically determine the proper treatment-signal format using at least part of said environmental-data received from an electronic tag associated with a treatment-control system.

5. A body and environment monitoring system as in claim 1, wherein said first computer is configured to:
   communicate with said at least one electronic tag scanning device;
      monitor said environmental-data and compare said environmental-data to predefined warning-criteria;
      issue a warning message when monitored environmental-data meets predefined warning-criteria; and
      wherein said warning message is issued to a local electronic device.

6. A body and environment monitoring system as in claim 5, wherein said first computer is configured to communicate with a remote computer and wherein said warning message is transmitted to said remote computer over at least one of a wired or wireless communications link.

7. A body and environment monitoring system as in claim 6, further comprising a display and wherein said warning message is at least one member from the group consisting of: (1) warning specific beep; (2) audio voice message; (3) flashing light; (3) message displayed on said display; (4) a tactile signal; (5) a mechanical vibration; and (4) message printed in Braille.

8. A body and environment monitoring system as in claim 7, wherein said first computer is further configured to accumulate reference data.

9. A body and environment monitoring system as in claim 8, wherein said display is configured to display at least one of said sensor-data, said environmental-data, said warning criteria and said reference data.

10. A body and environment monitoring system as in claim 1, wherein said first computer is configured to:

communicate with said at least one electronic tag scanning device;
communicate with a remote computer;
monitor said environmental-data and compare said environmental-data to predefined BREM-alert-criteria;
issue a BREM-alert when monitored environmental-data meets predefined BREM-alert-criteria; and
wherein said BREM-alert is issued to at least one of a local electronic device and a remote computer.

11. A body and environment monitoring system as in claim 10, wherein said first computer issues a timed warning message informing a user of a pending BREM-alert transmission and providing said user the opportunity to cancel said BREM-alert transmission.

12. A body and environment monitoring system as in claim 1, wherein a warning message is issued when environmental-data is detected by said least one electronic tag scanning device that meets predefined warning-criteria.

13. A body and environment monitoring system as in claim 12, further comprising a display configured to display at least one of said sensor-data, processed sensor-data, said environmental-data, processed environmental-data, said predefined warning-criteria and said warning message.

14. A body and environment monitoring system as in claim 13, wherein said warning message is at least one member from the group consisting of: (1) warning specific beep; (2) audio message; (3) flashing light; (3) message displayed on said display; and (4) message printed in Braille.

15. A body and environment monitoring system as in claim 1, wherein said body is a human body.

16. A body and environment monitoring system as in claim 15, wherein said at least one body-parameter is at least one member from the group consisting of: (1) body temperature; (2) blood pressure; (3) heart rate; (4) blood sugar level; (5) blood oxygen level; (6) cholesterol level; (7) respiration rate; (8) hormone level; (9) galvanic skin response; (10) EMG; (11) EEG; (12) EOG; (13) body fat; (14) hydration level (15) activity level; (16) body position; (17) UV radiation exposure; and (18) UV radiation absorption.

17. A body and environment monitoring system as in claim 1, wherein said at least one electronic tag scanning device is an RFID STR device and wherein said electronic tag is an RFID smart tag.

18. A body and environment monitoring system as in claim 17, wherein said RFID STR device is configured to listen for RFID smart tag signals and to transmit a RFID smart tag trigger signal when no RFID smart tag signals are detected.

19. A body and environment monitoring system as in claim 18, further comprising a display configured to display information received from at least one of said first computer and said REID STR device.

20. A body and environment monitoring system as in claim 19, wherein said display is further configured to display at least part of said sensor-data, wherein said sensor-data is at least one of real-time, near real-time data, processed sensor-data and unprocessed sensor-data.

21. A body and environment monitoring system as in claim 1, wherein said first computer is in wireless communication with a remote computer and wherein said remote computer is connected to at least one of a local area network and a wide area network.

22. A monitoring system comprising:
at least one electronic tag scanning device configured to transmit an electronic tag trigger signal and to receive electronic tag transmissions;
a first computer in communication with at least one electronic tag scanning device and configured to use said at least one electronic tag scanning device to retrieve environmental-data stored in electronic tags associated with items within an environment;
memory in communication with said first computer wherein said memory is at least one of a volatile memory and a non-volatile memory;
wherein said first computer stores retrieved environmental-data in said memory;
wherein said first computer is further configured to use said at least one electronic tag scanning device to transmit an electronic tag trigger signal when a predefined amount of time elapses without a valid electronic tag transmission being received containing valid environmental-data;
wherein said first computer and said at least one electronic tag scanning device is at least one of (a) mounted on a body, (b) attached to a body, and (c) carried by a body; and
at least one bio-sensor associated with a body and configured to generate sensor-data for at least one body-parameter, said first computer is in communication with said at least one bio-sensor and configured to retrieve sensor-data from said at least one bio-sensor and to store said sensor-data in said memory, said electronic tags remaining with their respective associated item within the environment such that said electronic tag scanning device retrieves the environmental-data upon coming within a predetermined range of said electronic tags, said stored environmental data relating to a characteristic of the associated item that is relevant to interpretation of the bio-sensor data.

23. A monitoring system as in claim 22, wherein said at least one electronic tag scanning device is an REID STR device and wherein said electronic tag is an RFID smart tag.

24. A monitoring system as in claim 23, wherein said environmental-data is at least one member from the group consisting of: (1) EMI Code; (2) item identification number; (3) item model number; (4) warning code; (5) room code; (6) floor code; (7) building code; (8) vehicle code; (9) meal code and (10) nutrition code.

25. A monitoring system as in claim 22, wherein said first computer is in communication with a remote computer.

26. A monitoring system as in claim 25, wherein said first computer is further configured to use said at least one electronic tag scanning device to transmit an electronic tag trigger signal according to transmit-criteria where said transmit-criteria is at least one member from the group consisting of: (1) periodically at set intervals; (2) periodically at random intervals; (3) upon manual request by a user; and (4) automatic request issued by said remote computer.

27. A monitoring system as in claim 22, wherein said first computer issues a warning message when retrieved environmental-data meets predefined warning-criteria.

28. A monitoring system as in claim 27, wherein said first computer is further configured to communicate with a remote computer and wherein said warning message is transmitted to said remote computer.

29. A monitoring system as in claim 27, further comprising a display in communication with said first computer and configured to display at least one of said environmental data and said warning message.

30. A monitoring system as in claim 29, wherein said display is at least one member from the group consisting of: (a) a display associated with a personal digital assistant; (b) LCD display associated with a watch; (c) a segmented display associated with a watch; (d) an LCD display associates with said first computer; (e) video-enabled glasses; (f) video-enabled goggles; (g) video-enabled helmets; (h) video-enabled room; and (i) video-enabled transparent surface.

31. A monitoring system as in claim 22, wherein said first computer is configured to automatically transmit treatment-signals when a monitored body-parameter meets predefined treatment-criteria.

32. A monitoring system as in claim 31, wherein said first computer is further configured to automatically format said treatment-signals based on environmental-data retrieved from electronic tags associated with a treatment control system near said body.

33. A monitoring system as in claim 32, wherein said first computer is further configured to accumulate reference data and wherein said display is further configured to display at least one of said reference data, said environmental-data, real-time sensor-data, near real-time sensor-data, processed sensor-data and unprocessed sensor-data.

34. A body and environment monitoring system as in claim 33, wherein said sensor data is transmitted to a remote computer.

35. A body and environment monitoring system comprising:
- at least one bio-sensor associated with a body and configured to generate sensor-data for at least one body-parameter;
- at least one electronic tag scanning device associated with said body and configured to receive electronic tag transmissions comprising environmental-data stored in electronic tags associated with items in an environment, said electronic tags remaining with their respective associated item within the environment such that said electronic tag scanning device retrieves the environmental-data when the monitored body comes within a predetermined range of said electronic tags, said stored environmental data relating to a characteristic of the associated item that is relevant to interpretation of the bio-sensor data;
- a first computer associated with said body and in communication with said at least one bio-sensor and said at least one electronic tag scanning device;
- said first computer configured to receive said sensor-data and said environmental-data; and
- a memory in communication with said first computer wherein said memory is configured to store said sensor-data and said environmental-data.

36. A body monitoring system as in claim 35, said first computer further configured to generate treatment-signals and to transmit said treatment-signals to a treatment control system when said first computer determines that a body-parameter meets predefined treatment-criteria; and
- said first computer further configured to automatically determine the proper treatment-signal format based at least in part on at least one of said environmental-data and treatment-control-system-information retrieved from said treatment control system.

37. A body monitoring system as in claim 36, wherein said treatment control system is at least one of a pharmaceutical treatment control system and a therapeutic treatment control system.

38. A body monitoring system as in claim 37, wherein said treatment-signal is transmitted over at least one of a wired or wireless communication link.

39. A body monitoring system as in claim 35, wherein said at least one electronic tag scanning device is an RFID STR device and wherein said electronic tag is an REID smart tag.

* * * * *